United States Patent
Yacoub et al.

(10) Patent No.: US 11,172,961 B2
(45) Date of Patent: Nov. 16, 2021

(54) ORTHOPEDIC FIXATION DEVICES AND METHODS OF INSTALLATION THEREOF

(71) Applicant: GLOBUS MEDICAL, INC., Audubon, PA (US)

(72) Inventors: George Yacoub, Egg Harbor Township, NJ (US); Jeff Nichols, Philadelphia, PA (US); David Leff, Philadelphia, PA (US)

(73) Assignee: Globus Medical Inc., Audubon, PA (US)

( * ) Notice: Subject to any disclaimer, the term of this patent is extended or adjusted under 35 U.S.C. 154(b) by 2 days.

(21) Appl. No.: 15/975,097

(22) Filed: May 9, 2018

(65) Prior Publication Data

US 2018/0325558 A1  Nov. 15, 2018

Related U.S. Application Data

(63) Continuation-in-part of application No. 15/433,003, filed on Feb. 15, 2017, which is a continuation of application No. 14/692,880, filed on Apr. 22, 2015, now Pat. No. 9,603,635, which is a continuation-in-part of application No. 14/221,788, filed on Mar. 21, 2014, now Pat. No. 9,186,187, (Continued)

(51) Int. Cl.
*A61B 17/70* (2006.01)
*A61B 17/88* (2006.01)
*A61B 17/68* (2006.01)

(52) U.S. Cl.
CPC ...... *A61B 17/7034* (2013.01); *A61B 17/7001* (2013.01); *A61B 17/7004* (2013.01); *A61B 17/705* (2013.01); *A61B 17/7011* (2013.01); *A61B 17/7032* (2013.01); *A61B 17/7035* (2013.01); *A61B 17/7037* (2013.01); *A61B 17/7047* (2013.01); *A61B 17/7056* (2013.01); *A61B 17/7082* (2013.01); *A61B 17/8816* (2013.01); *A61B 2017/681* (2013.01)

(58) Field of Classification Search
CPC ............ A61B 17/7082; A61B 17/7034; A61B 17/7037; A61B 17/7001; A61B 17/7004; A61B 17/7011; A61B 17/7047; A61B 17/705; A61B 17/7056; A61B 17/8816; A61B 2017/681
USPC ....... 606/246, 250, 253, 264–270, 276, 277, 606/278
See application file for complete search history.

(56) References Cited

U.S. PATENT DOCUMENTS 5,487,744 A * 1/1996 Howland ........... A61B 17/7041 606/264
5,716,356 A   2/1998 Biedermann et al.
(Continued)

FOREIGN PATENT DOCUMENTS

DE  9314297 U1  5/1994
EP  1459690 A1  9/2004
(Continued)

*Primary Examiner* — Eduardo C Robert
*Assistant Examiner* — David C Comstock

(57) ABSTRACT

The present invention is generally directed to orthopedic fixation devices that comprise a pre-assembled double headed tulip assembly, having two tulip elements to receive rods, wherein the assembly may be configured to receive a bone fastener in at least one of the tulip elements. At least one of the tulip elements may comprise a saddle and a ring to attach the double headed tulip to a bone fastener.

19 Claims, 44 Drawing Sheets

Related U.S. Application Data which is a continuation-in-part of application No. 13/731,436, filed on Dec. 31, 2012, now Pat. No. 9,198,694, which is a continuation-in-part of application No. 13/183,965, filed on Jul. 15, 2011, now Pat. No. 8,888,827.

(56) References Cited

U.S. PATENT DOCUMENTS

| | | |
|---|---|---|
| 6,485,491 B1 | 11/2002 | Farris et al. |
| 6,695,846 B2 | 2/2004 | Richelsoph et al. |
| 7,678,136 B2 | 3/2010 | Doubler et al. |
| 8,221,457 B2 | 7/2012 | Delecrin et al. |
| 8,435,266 B2 | 5/2013 | Richelsoph |
| 8,657,857 B2 | 2/2014 | Dall et al. |
| 9,055,980 B2 | 6/2015 | Biedermann |
| 9,615,867 B2 | 4/2017 | Picetti et al. |
| 9,820,780 B2 | 11/2017 | Duncan et al. |
| 2002/0035366 A1 | 3/2002 | Walder et al. |
| 2004/0267264 A1 | 12/2004 | Konieczynski et al. |
| 2005/0171537 A1 | 8/2005 | Mazel et al. |
| 2005/0228385 A1 | 10/2005 | Iott et al. |
| 2006/0079892 A1 | 4/2006 | Roychowdhury et al. |
| 2008/0091213 A1* | 4/2008 | Jackson .............. A61B 17/7082 606/99 |
| 2008/0114362 A1 | 5/2008 | Justis et al. |
| 2008/0294202 A1 | 11/2008 | Peterson et al. |
| 2010/0152787 A1 | 6/2010 | Walsh et al. |
| 2011/0040335 A1 | 2/2011 | Stihl et al. |
| 2011/0098755 A1* | 4/2011 | Jackson .............. A61B 17/7008 606/305 |
| 2011/0106173 A1 | 5/2011 | Lindemann et al. |
| 2011/0160779 A1 | 6/2011 | Schlaepfer et al. |
| 2012/0071926 A1 | 3/2012 | Jani et al. |
| 2013/0144346 A1* | 6/2013 | Jackson .............. A61B 17/8605 606/305 |
| 2014/0121703 A1* | 5/2014 | Jackson ............... A61B 17/702 606/246 |
| 2015/0223844 A1 | 8/2015 | Leff et al. |
| 2015/0359568 A1 | 12/2015 | Rezach |
| 2016/0302831 A1 | 10/2016 | Nichols et al. |
| 2016/0331413 A1* | 11/2016 | Daniels ............. A61B 17/7032 |
| 2017/0095271 A1 | 4/2017 | Faulhaber |
| 2017/0311985 A1 | 11/2017 | Bobbitt et al. |
| 2018/0014863 A1 | 1/2018 | Biester et al. |
| 2018/0228516 A1* | 8/2018 | Armstrong ......... A61B 17/8665 |
| 2021/0022779 A1* | 1/2021 | Bobbit ............... A61B 17/7034 |

FOREIGN PATENT DOCUMENTS

| | | |
|---|---|---|
| FR | 2720262 A1 | 12/1995 |
| WO | 2017069930 A2 | 4/2017 |

* cited by examiner

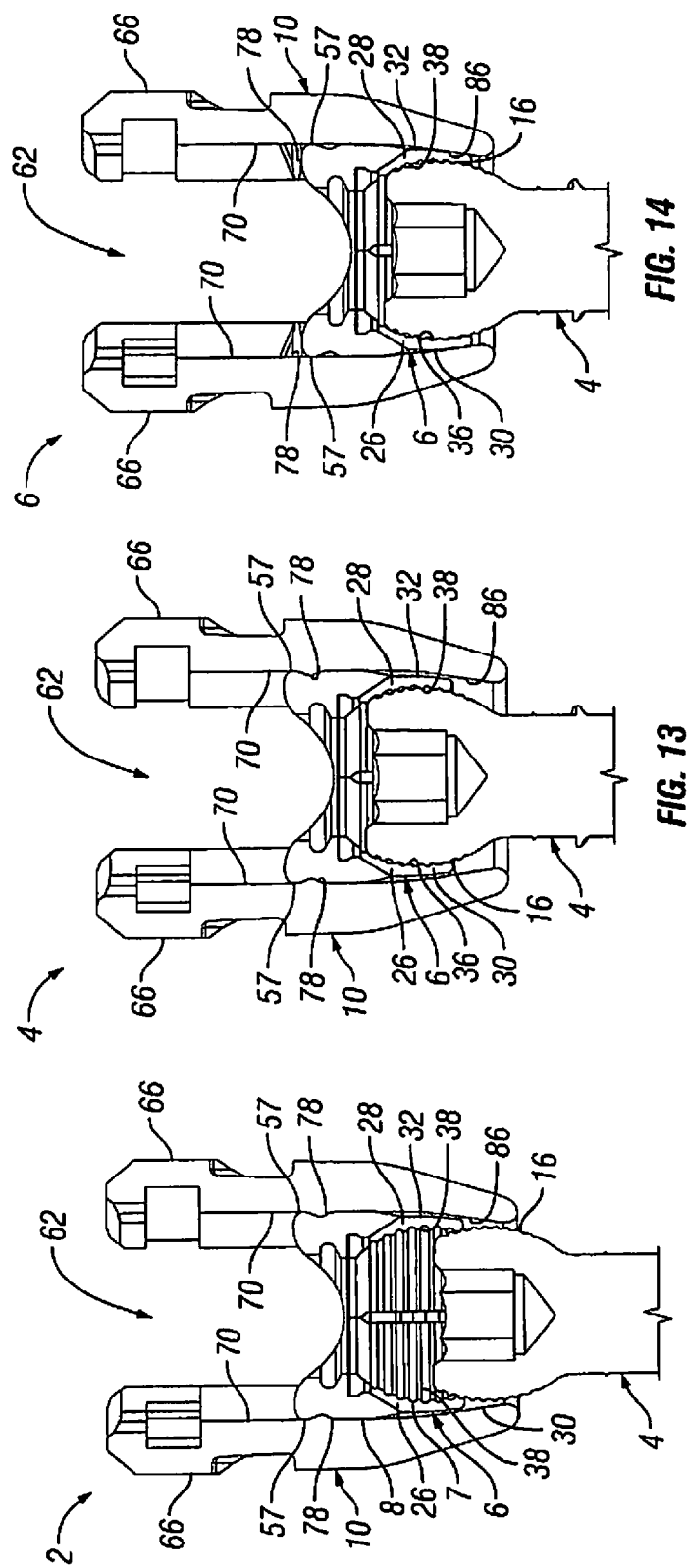

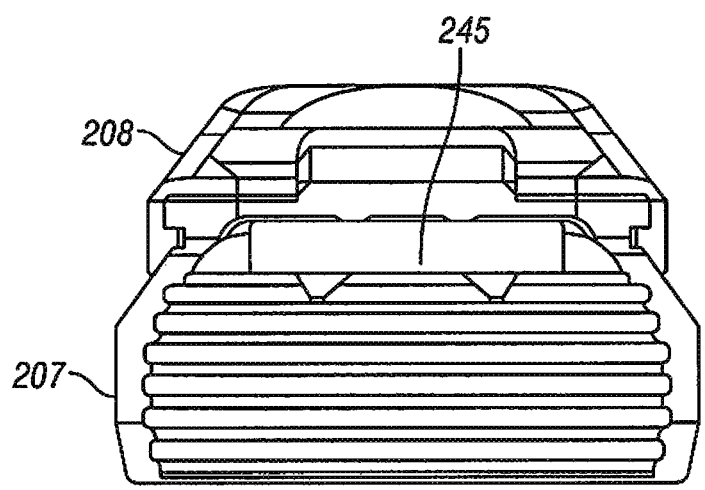
FIG. 36
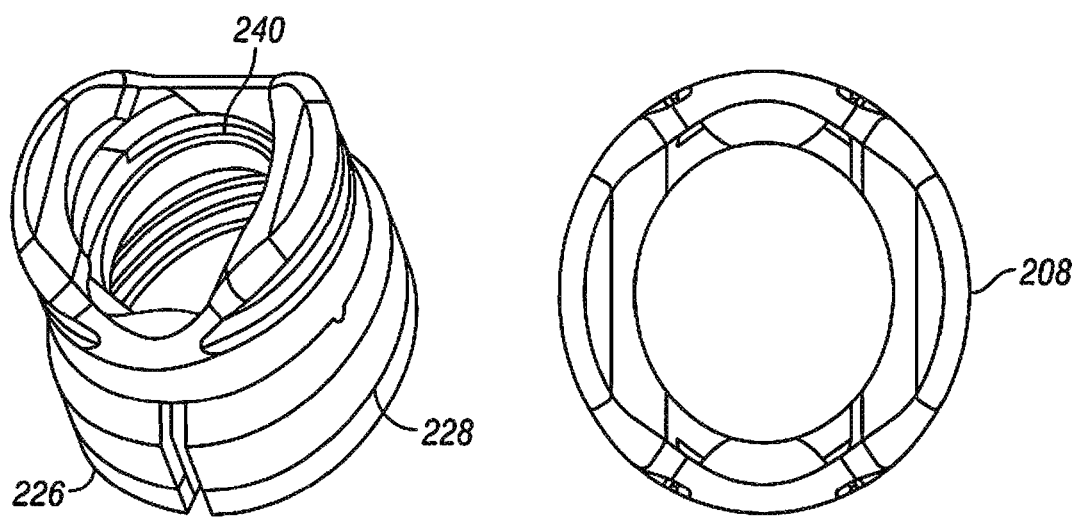
FIG. 37
FIG. 38

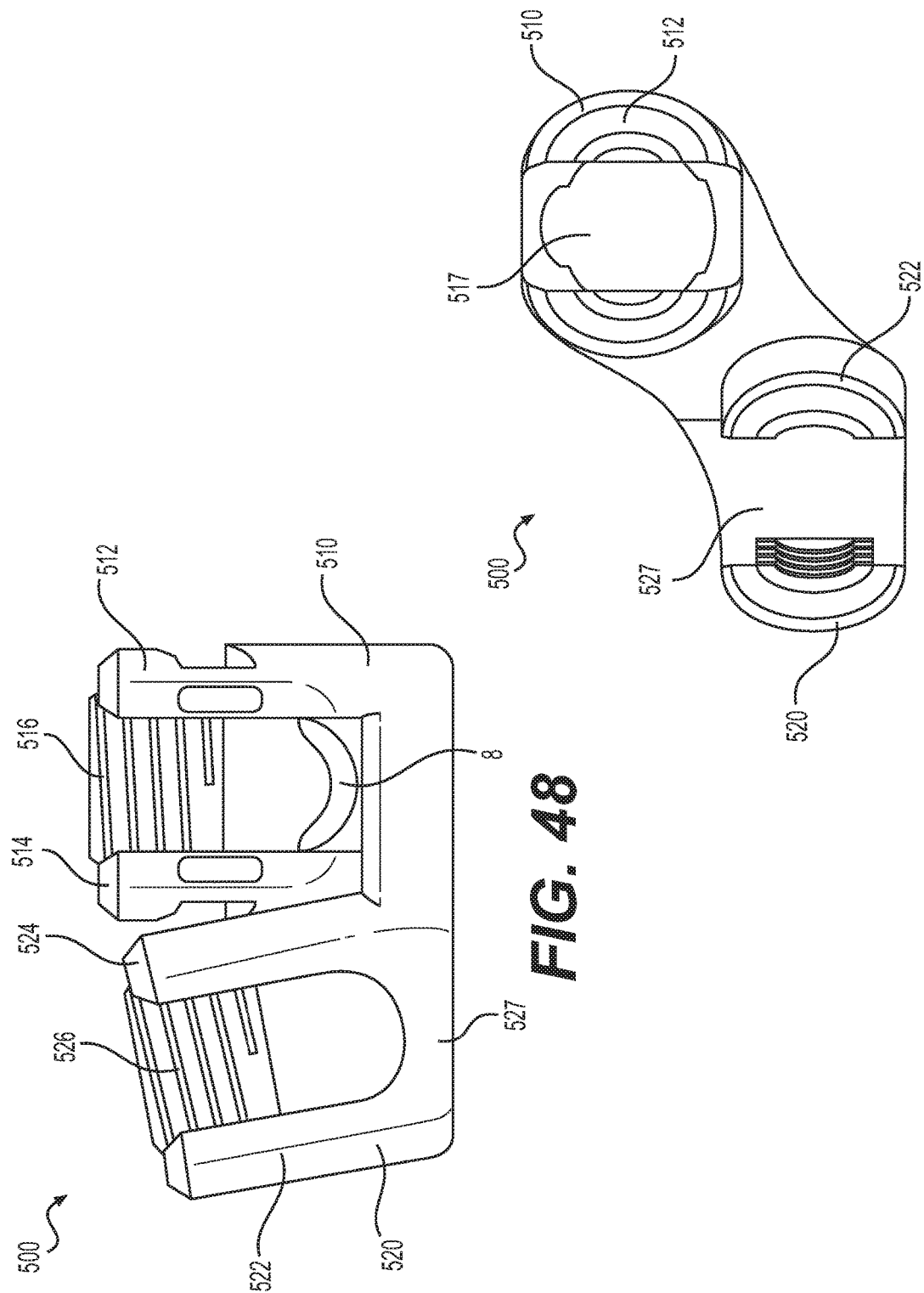

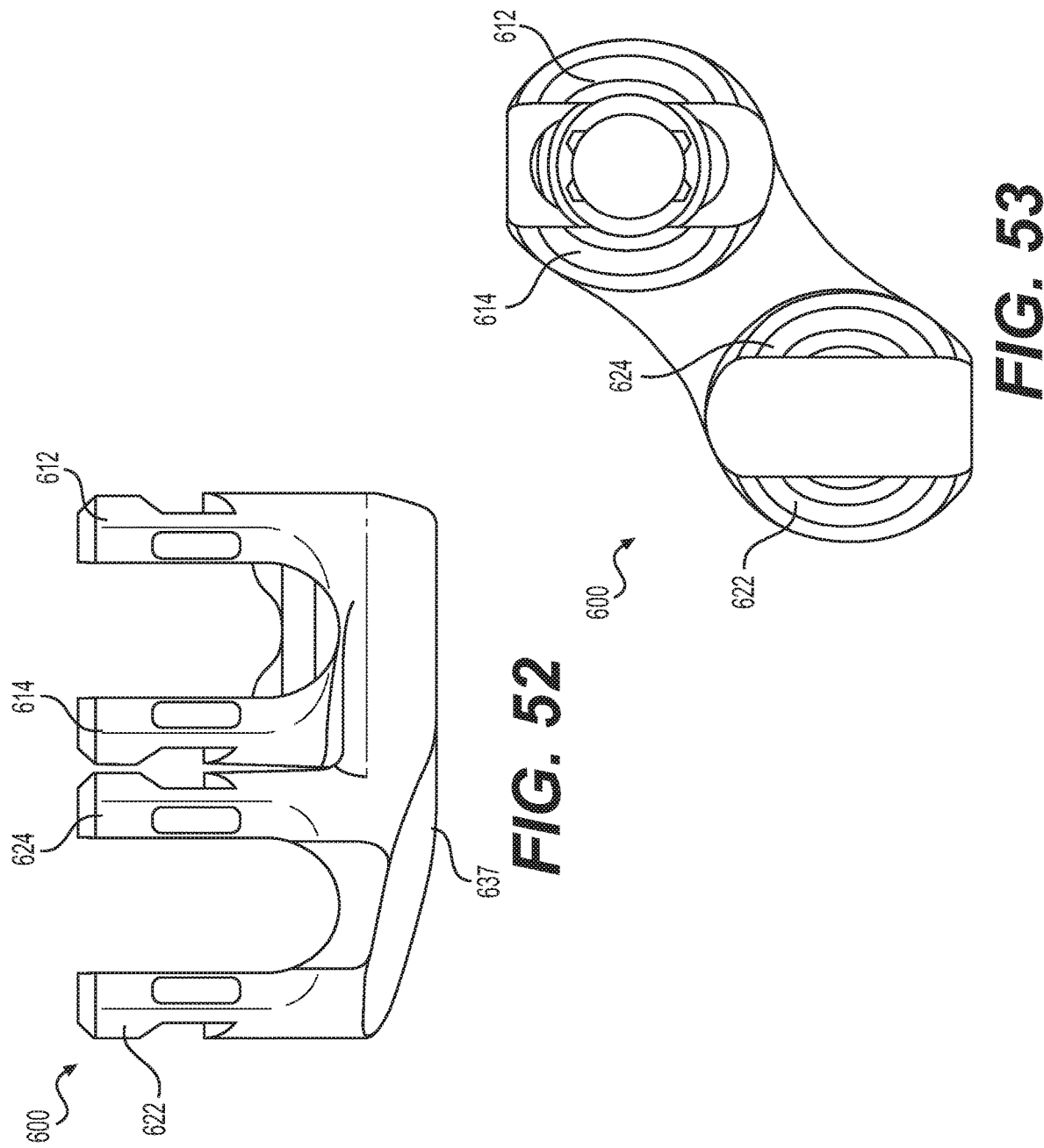

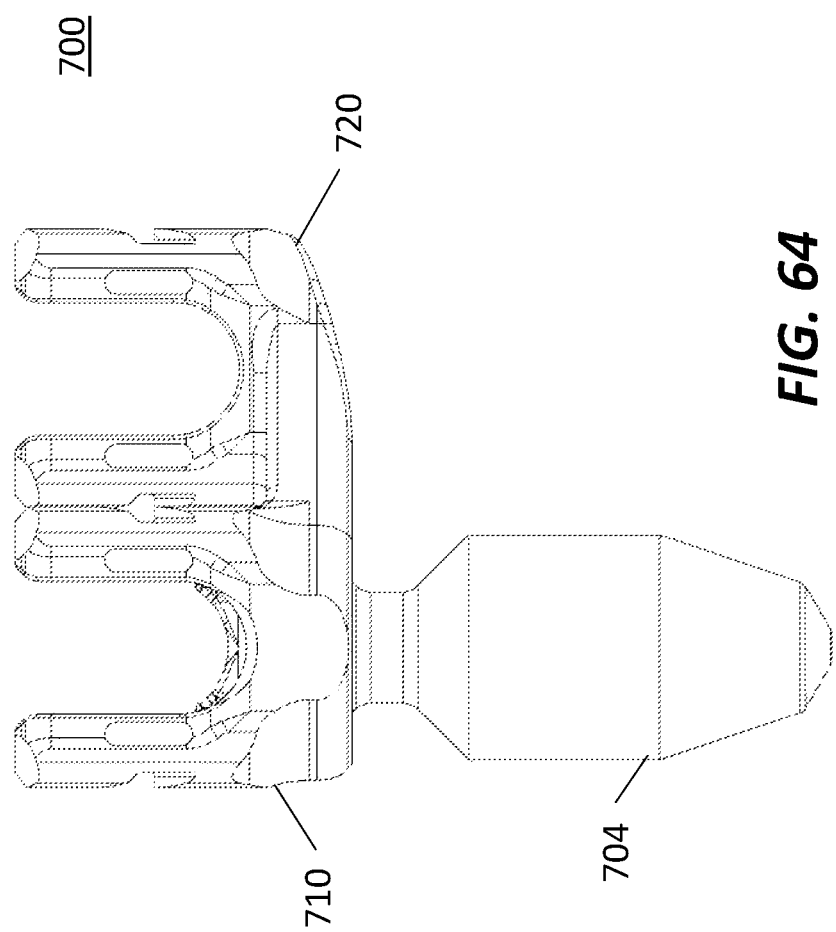

ORTHOPEDIC FIXATION DEVICES AND METHODS OF INSTALLATION THEREOF

CROSS REFERENCE TO RELATED APPLICATIONS

This patent application is a continuation-in-part of U.S. Ser. No. 15/433,003, filed on Feb. 15, 2017, titled "Orthopedic Fixation Device and Methods of Installation Thereof," published as U.S. Pat. Pub. No. 2017-0224386, which is a continuation of U.S. Ser. No. 14/692,880, filed Apr. 22, 2015, titled "Orthopedic Fixation Device and Methods of Installation Thereof," now issued as U.S. Pat. No. 9,603,635, which is a continuation-in-part application of U.S. Ser. No. 14/221,788, filed Mar. 21, 2014, titled "Orthopedic Fixation Devices and Methods of Installation Thereof," now issued as U.S. Pat. No. 9,186,187, which is a continuation-in-part application of U.S. patent application Ser. No. 13/731,436, filed on Dec. 31, 2012, titled "Orthopedic Fixation Devices and Methods of Installation Thereof," now issued as U.S. Pat. No. 9,198,694, which is a continuation-in-part application of U.S. patent application Ser. No. 13/183,965, filed on Jul. 15, 2011, now issued as U.S. Pat. No. 8,888,827, titled "Orthopedic Fixation Devices and Methods of Installation Thereof," all of which are herein incorporated by reference in their entirety.

FIELD OF THE INVENTION

The present invention relates to orthopedic fixation devices, and, in one or more embodiments, to an orthopedic fixation device configured to receive multiple elongated rods for attachment to adjacent vertebrae.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of fixation devices to one or more vertebrae and connecting the devices to an elongate rod that generally extends in the direction of the axis of the spine.

Treatment for these spinal irregularities often involves using a system of fixation devices to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, a fixation device along with a vertical solid member can help restore spinal elements to a pain free situation, or at least may help reduce pain or prevent further injury to the spine.

Typically, fixation devices may include a bone fastener (e.g., bone screw, hook, etc.) for coupling the fixation device to vertebra. Fixation devices further may include a tulip element for coupling the bone fastener to the elongated rod. Clamp and/or wedge elements may be used to secure the bone fastener in the tulip element. The bone fastener may be retained in the fixation device via a ring that is disposed within the tulip and underneath the bone fastener. A locking cap may be used to secure the rod in the tulip element.

While in some circumstances a fixation device containing a single tulip member may be sufficient for fixation, there may be circumstances that the fixation device be able to accommodate multiple elongated rods. This may be a concern where more stability between adjacent fixation devices is required. Accordingly, there exists a need for new and improved orthopedic fixation devices.

SUMMARY OF THE INVENTION

In an exemplary embodiment, the present invention provides an orthopedic fixation device. The orthopedic fixation device may comprise a coupling element, the coupling element may comprise a bore there through and an interior surface disposed about the bore. The orthopedic fixation device further may comprise a bone fastener, wherein the bone fastener comprises a head and an extension that extends from the head, wherein the head is configured for loading into the coupling element through the bottom of the bore. The orthopedic fixation device further may comprise a locking clamp assembly. The locking clamp assembly may comprise a clamp element, wherein the clamp element comprises a first clamp portion and a second clamp portion, wherein the first and second clamp portions each have an outer surface and an inner surface, wherein at least a portion of the outer surface is configured to engage the interior surface of the coupling element, and wherein at least a portion of the inner surface is configured to engage the head of the bone fastener. The locking clamp assembly further may comprise a wedge element, wherein the wedge element comprises a wedge bore configured to receive an upper portion of the clamp element and an inner wedge surface disposed around at least a lower portion of the wedge bore, wherein the inner wedge surface is configured to engage at least portion of the outer surface of the first and second clamp portions.

The present disclosure may also provide a pre-assembled spine stabilization system including a first bone fastener, a second bone fastener, a first tulip assembly, and second tulip assembly. The first tulip assembly may include a first tulip element, having a first saddle and a first ring, and a second tulip element. The first tulip element of the first tulip assembly may be configured to be received over the first bone fastener. The second tulip assembly may include a first tulip element having a second saddle and a second ring, and a second tulip element. The first tulip element of the second tulip assembly may be configured to be received over the second bone fastener. The spine stabilization system may include a first rod member that extends from the first tulip assembly to the second tulip assembly. The first rod member may be disposed on the first saddle and the second saddle. The spine stabilization system may include a second rod member that extends from the first tulip assembly to the second tulip assembly. The first bone fastener may be retained in the first tulip assembly via the first ring and the second bone fastener may be retained in the second tulip assembly via the second ring.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 12-14 illustrate an alternative orthopedic fixation device in accordance with embodiments of the present invention;

FIG. 36 illustrates an alternate side view of the wedge element mated with the clamp element in FIG. 35;

FIG. 37 illustrates a top perspective view of the wedge element mated with the clamp element in FIG. 35;

FIG. 38 illustrates a top view of a wedge element in accordance with embodiments of the present invention;

FIG. 48 illustrates a front view of the modular double tulip assembly of FIG. 47;

FIG. 49 illustrates a top view of the modular double tulip assembly of FIG. 47;

FIG. 52 illustrates a front view of the modular double tulip assembly of FIG. 51;

FIG. 53 illustrates a top view of the modular double tulip assembly of FIG. 51;

FIGS. 62-64 illustrate side views of the dual rod construct using a pre-assembled double headed tulip assembly of FIG. 56 in accordance with embodiment of the present disclosure.

DETAILED DESCRIPTION OF THE EMBODIMENTS

Embodiments of the present invention are generally directed to orthopedic fixation devices configured for bottom loading of the bone fastener. Instead of loading the bone fastener from the top of the tulip element, embodiments of the present invention load the bone fastener from the bottom of the tulip element. With the bone fastener loaded in the tulip element, a locking clamp assembly can then be used to secure the bone fastener therein. Thus, unlike prior orthopedic fixation devices, embodiments of the present invention permit the use of larger bone fasteners without having to also increase the size of the tulip element. This should, for example, reduce the needed inventory, decreasing the necessary graphic cases needed to perform a similar procedure, while decreasing in-house inventory costs.

Further, as explained by the examples and illustrations below, the bone fastener of the orthopedic fixation devices can be placed in the vertebra without the tulip element in accordance with embodiments of the present invention. The tulip element can then be attached to the bone fastener in situ. This should reduce the material in the surgical wound, thus increasing visualization for disc preparation and interbody procedures, for example. The bone fastener can also be used to distract or otherwise manipulate the surgical site, further increasing visualization and ease of surgery, for example. Additionally, site preparation can be performed, in some embodiments, after the bone fastener has been placed, which may allow for more accurate pedicle decortication.

Figure 1:
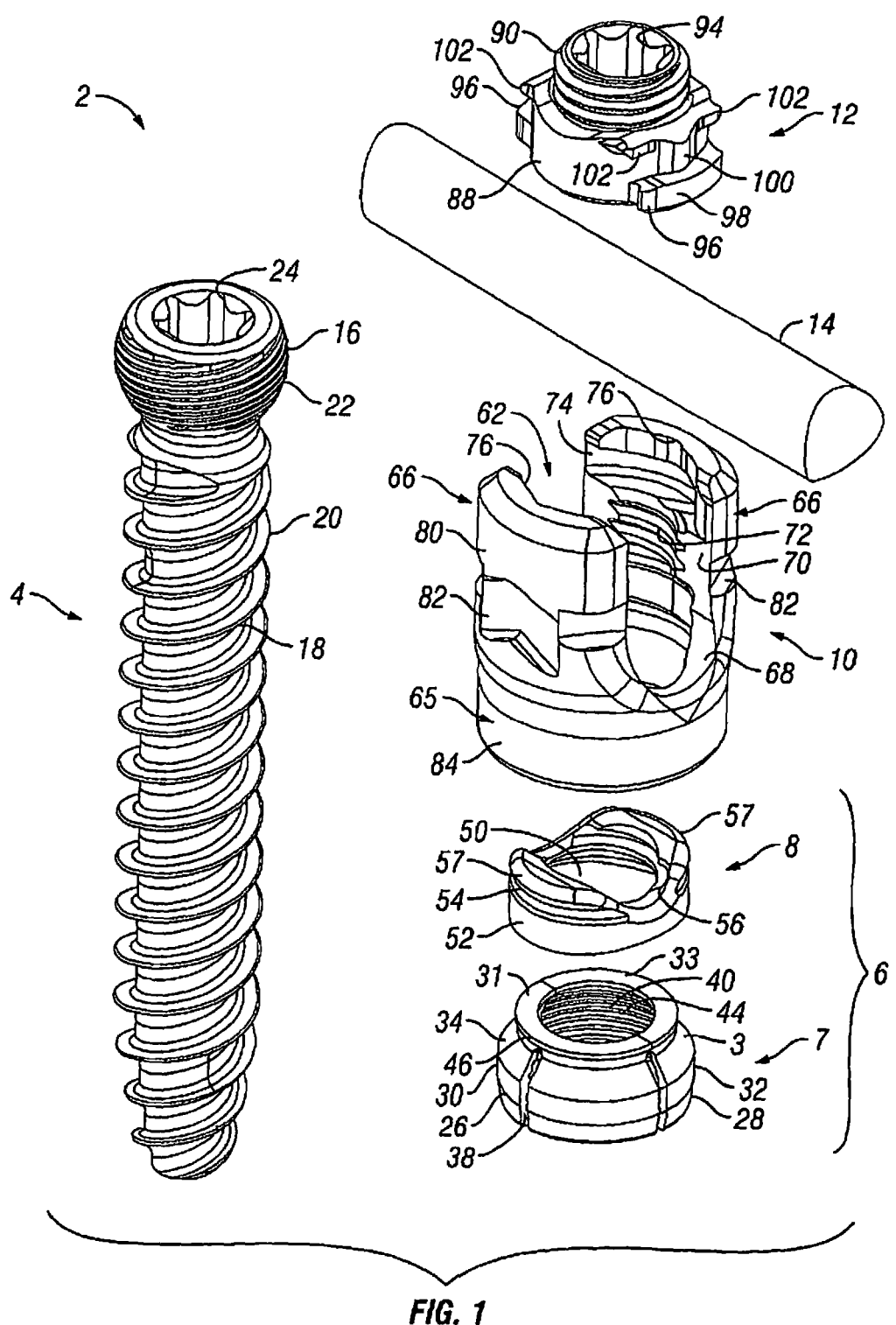
FIG. 1 is an exploded view of an orthopedic fixation device in accordance with embodiments of the present invention.

Turning now to FIG. 1, an exploded view of an orthopedic fixation device 2 is illustrated in accordance with embodiments of the present invention. As illustrated, the orthopedic fixation device 2 may comprise a bone fastener 4, a locking clamp assembly 6 (which may comprise, for example, a clamp element 7 and a wedge element 8), a tulip element 10, and a locking cap assembly 12. As will be discussed in more detail below, the bone fastener 4 may be loaded from the bottom of the tulip element 10 with the locking clamp assembly 6 already loaded therein. Prior to being locked into place, the tulip element 10 can be moved and rotated into a plurality of positions with respect to the bone fastener 4. Once the tulip element 10 is at the desired position with respect to the bone fastener 4, the tulip element 10 may be locked onto the bone fastener 4. In the illustrated embodiment, the locking cap assembly 12 is configured to secure a rod 14 in the tulip element 10. In one embodiment, the tulip element 10 is fixed onto the bone fastener 4 contemporaneously with securing of the rod 14 in the tulip element 10.

As illustrated by FIG. 1, the bone fastener 4 includes a head 16 and a shaft 18 that extends from the head 16. The illustrated embodiment shows the shaft 18 having a tapered shape and threads 20. Those of ordinary skill in the art will appreciate that the shaft 18 may have a number of different features, such as thread pitch, shaft diameter to thread diameter, overall shaft shape, and the like, depending, for example, on the particular application. While the head 16 may have any general shape, at least a portion of the head 16 may have a curved surface in order to allow for rotational movement or angular adjustment of the bone fastener 4 with respect to the tulip element 10. For example, at least a portion of the head 16 may be shaped to form a portion of a ball or at least a portion of a sphere. As illustrated, the head 16 may have a roughened or textured surface 22 that improves engagement with the clamp element 7. In certain embodiments, the head 16 may have a tool engagement surface, for example, that can be engaged by a screw-driving tool or other device. The tool engagement surface can permit the physician to apply torsional or axial forces to the bone fastener 4 to drive the bone fastener 4 into the bone. In the illustrated embodiment, the tool engagement surface of the head 16 is a polygonal recess 24. For instance, the polygonal recess 24 may be a hexagonal recess that receives a hexagonal tool, such as an allen wrench, for example. The present invention is intended to encompass tool engagement surfaces having other shapes, such as slot or cross that may be used, for example, with other types of screwdrivers. In an alternative embodiment (not illustrated), the engagement surface may be configured with a protruding engagement surface that may engage with a tool or device having a corresponding recess.

Figure 2:
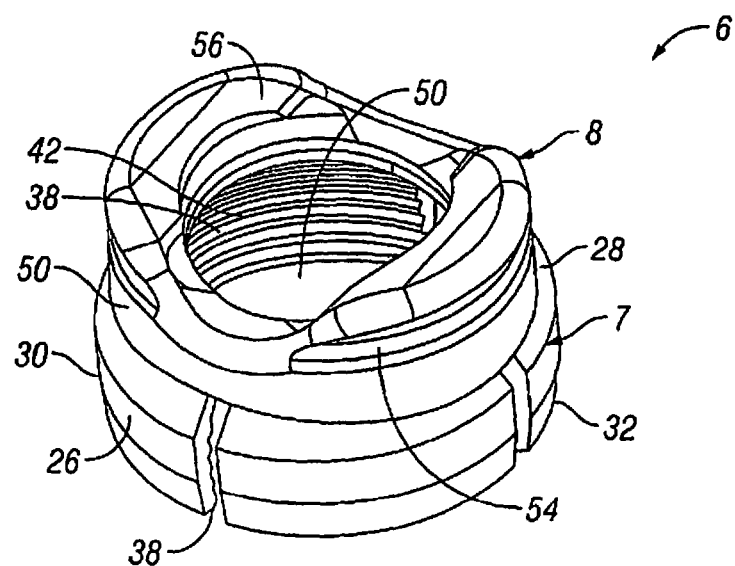
FIG. 2 is a perspective view of a locking clamp assembly in accordance with embodiments of the present invention.
Figure 3:
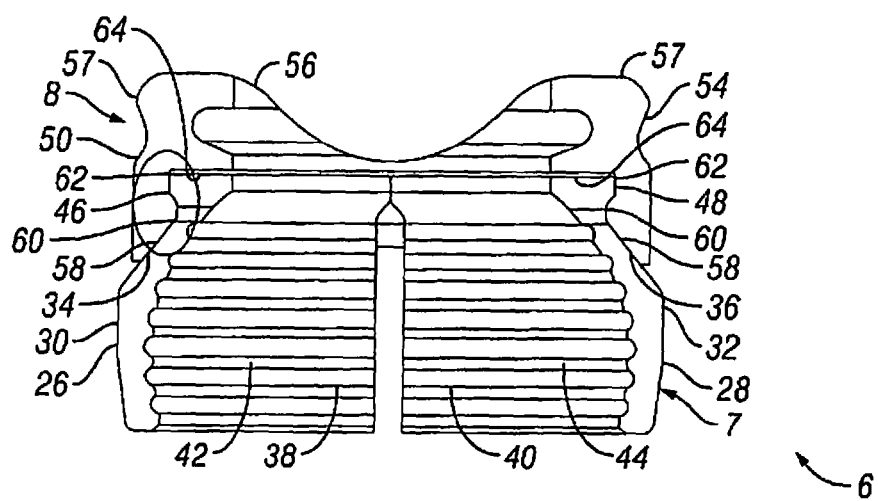
FIG. 3 is a cross-sectional view of a locking clamp assembly in accordance with embodiments of the present invention.

Referring now to FIGS. 1-3, clamp element 7 of the locking clamp assembly 6 will be described in more detail in accordance with embodiments of the present invention. As illustrated, the clamp element 7 includes a first clamp portion 26 and a second clamp portion 28. In the illustrated embodiment, the first clamp portion 26 is substantially identical to and a mirror image of, the second clamp portion 28. The first and second clamp portions 26, 28 provide a collar about the head 16 of the bone fastener 4, when installed, as discussed in more detail below. The first and second clamp portions 26, 28 grip bone fastener 4 when force is applied onto the clamp element 7 by the tulip element 10. While the embodiments that are described and illustrated generally describe the first and second clamp portions 26, 28 as substantially identical, the portions 26, 28 may be of varying size and are not required to be mirror images of one another. In addition, while the clamp element 7 is illustrated as having two clamp portions (first and second clamp portions 26, 28), the clamp element 7 may comprise more than two portions for gripping the bone fastener 4.

As illustrated, each of the first and second clamp portions 26, 28 includes an outer surface 30, 32, which may be curved or rounded, as best shown in FIGS. 1 and 2. The outer surfaces 30, 32 of the first and second clamp portions 26, 28 may each include an outer tapered surface 34, 36. In addition, the outer surfaces 30, 32 may each also have at least one slit 38 formed therein. The at least one slit 38 may, for example, allow the first and second clamp portions 26, 28 to constrict and securely engage the head 16 of the bone fastener 4. The outer surfaces 30, 32 should abut and engage the inner wedge surface 86 of the tulip element 10 when fully installed and locked in place in the tulip element 10 in accordance with present embodiments. With particular reference to FIG. 3, the first and second clamp portions 26, 28 each include inner surfaces 38, 40. When fully installed and locked in place in the tulip element 10, the inner surfaces 38, 40 should abut and engage the head 16 of the bone fastener 4 in accordance with present embodiments. The illustrated embodiment shows the inner surfaces 38, 40 having roughened or textured features 22 that improve engagement with the head 16 of the bone fastener 4. The first and second clamp portions 26, 28 each may also include an external lip 46, 48, which may be located above the outer tapered surfaces 34, 36, as best seen in FIG. 3. The first and second clamp portions 26, 28 each may also include an upper surface 31, 33, as best seen in FIG. 1.

Figure 4:
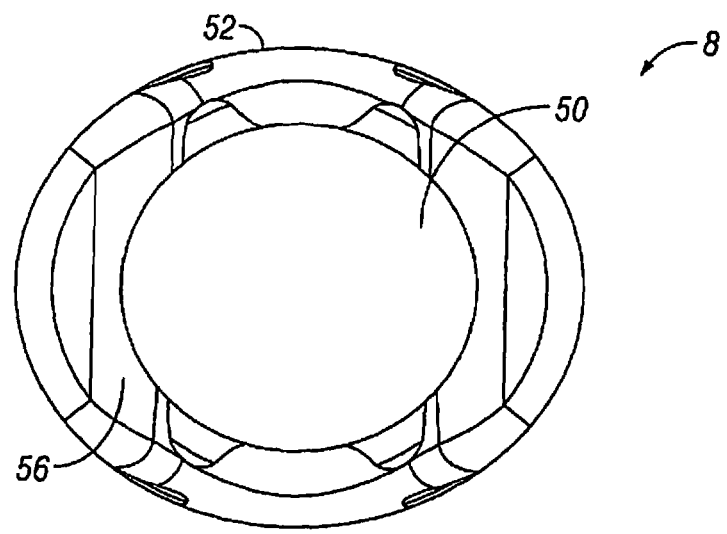
FIG. 4 is a top view of a wedge element in accordance with embodiments of the present invention.
Figure 5:
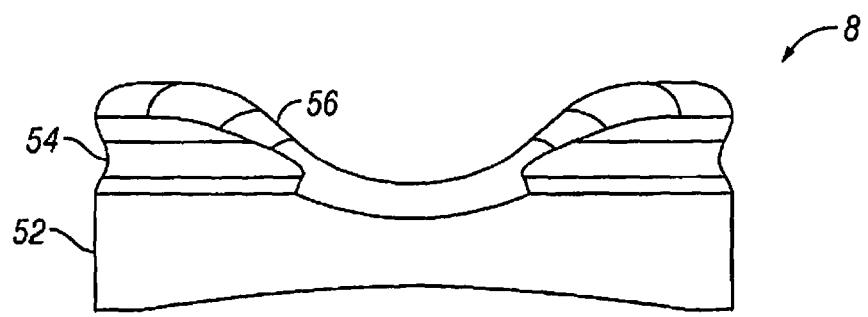
FIG. 5 is a side view of a wedge element in accordance with embodiments of the present invention.

Referring now to FIGS. 1-5, the wedge element 8 of the locking clamp assembly 6 will be described in more detail in accordance with embodiments of the present invention. As illustrated, the wedge element 8 may include a bore 50. The lower portion of the bore 50 may be sized to receive the upper portion of the clamp element 7, including external lips 46, 48 of the first and second clamp portions 26, 28. The wedge element further may include an outer surface 52 having a recessed portion 54. The outer surface 52 may be generally rounded, for example. As best seen in FIG. 4, the outer surface 52 of the wedge element 8 may be generally elliptical, in one embodiment. The elliptical shape of the outer surface 52 should, for example, limit radial motion of the wedge element when installed in the tulip element 10. The wedge element 8 further may include an upper surface 56. In the illustrated embodiment, the upper surface 56 defines a seat that receives the rod 14. As illustrated, the upper surface 56 may be generally convex in shape. In the illustrated embodiment, the wedge element 8 further includes an upper lip 57.

With particular reference to FIG. 3, the wedge element 8 further includes an inner wedge surface 58. As illustrated, the inner wedge surface 58 may be disposed around a lower portion of the bore 50. In one embodiment, the inner wedge surface 58 forms a conical wedge. The inner wedge surface 58 operates, for example, to engage the outer tapered surfaces 34, 36 of the first and second clamp portions 26, 28 to force the clamp element 7 down the bore 62 of the tulip element 10. The wedge element 8 further may include an inner protruding surface 60 adjacent to the inner wedge surface 58 and an inner recessed surface 62 adjacent the inner protruding surface 60. The wedge element 8 further may include an inner seat 64. As illustrated, the inner seat 64 may be downwardly facing for receiving upper surfaces 31, 33 of the first and second clamp portions 26, 28. In an embodiment, the inner seat 64 restricts or limits movement of the clamp element 4 through the bore 50 of the wedge element 8.

In accordance with present embodiments, the locking clamp assembly 6 can be assembled prior to insertion into the tulip element 10. In one embodiment, for assembly, the clamp element 7 may be inserted into the wedge element 8 upwardly through the bore 50. The outer surfaces 30, 32 of the first and second clamp portions 26, 28 should slidingly engage the inner wedge surface 58 of the wedge element 8 as the clamp element 7 is inserted. The clamp element 7 should be inserted until the external lips 46, 48 of the first and second clamp portions 26, 28 pass the inner protruding surface 60 of the wedge element 8. The inner protruding surface 60 engages the external lips 46, 48 to secure the clamp element 7 in the wedge element 8. In the illustrated embodiment, the locking clamp assembly 6 will not fit downwardly through the top of the bore 62 of the tulip element 10 as the locking clamp assembly has an outer diameter at its biggest point that is larger than the inner diameter of the upper portion of the bore 62.

Figure 6:
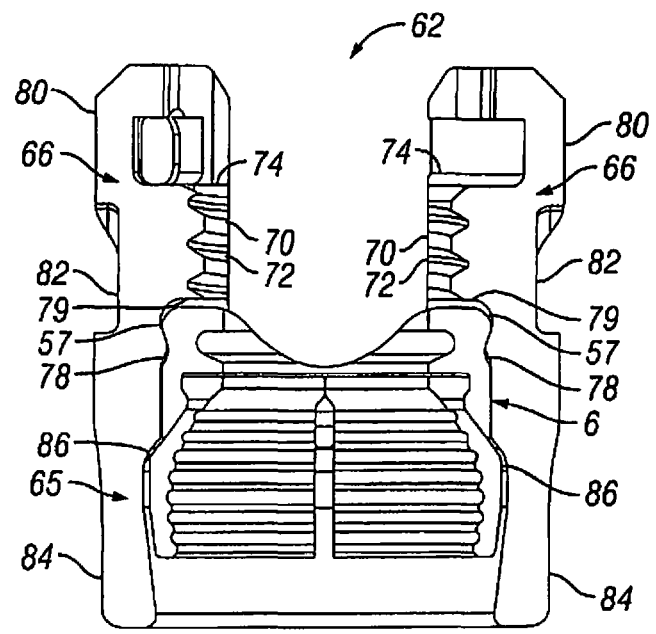
FIG. 6 is a cross-sectional view of a locking clamp assembly disposed in a tulip element in an unlocked configuration in accordance with embodiments of the present invention.
Figure 9:
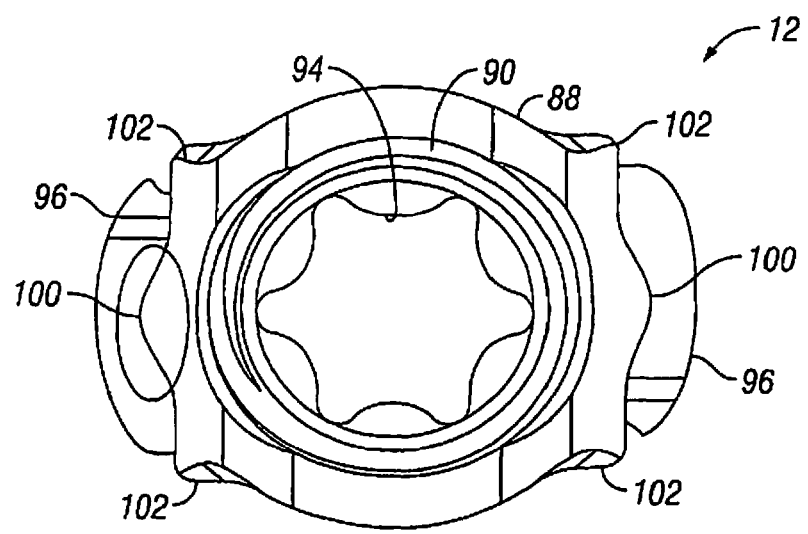
FIG. 9 is a top view of a locking cap assembly in accordance with embodiments of the present invention.
Figure 8:
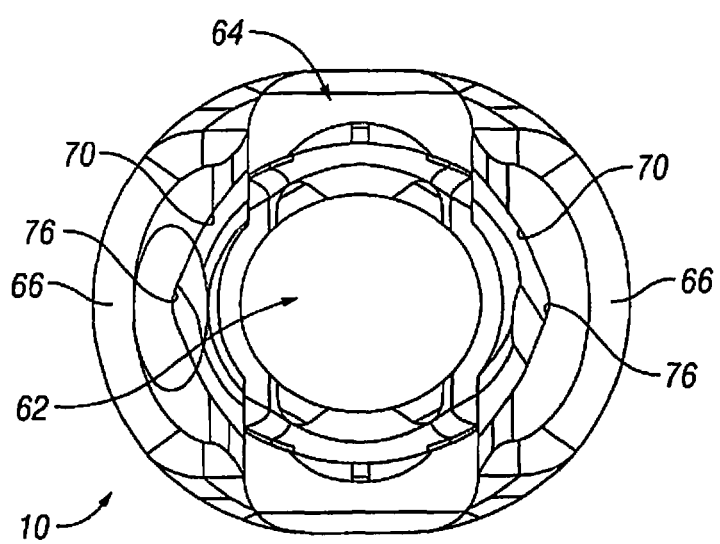
FIG. 8 is a top view of a tulip element in accordance with embodiments of the present invention.
Figure 10:
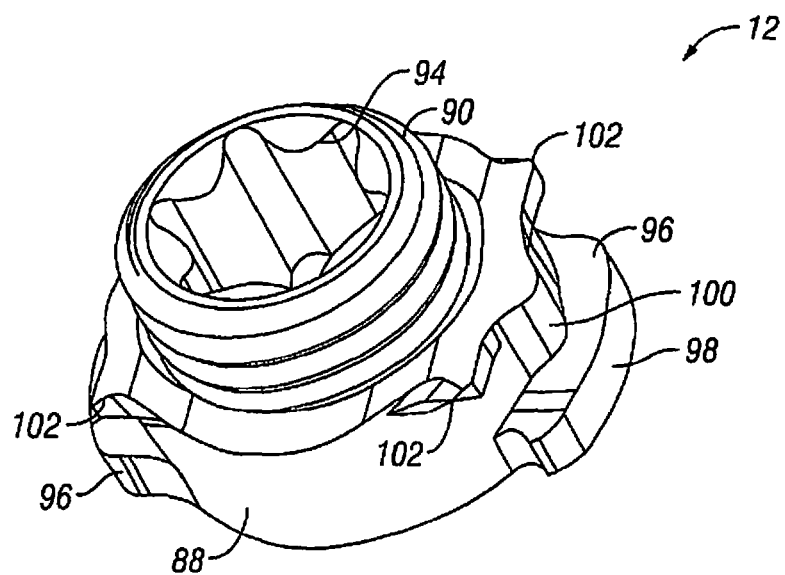
FIG. 10 is a perspective view of a locking cap assembly in accordance with embodiments of the present invention.
Figure 11:
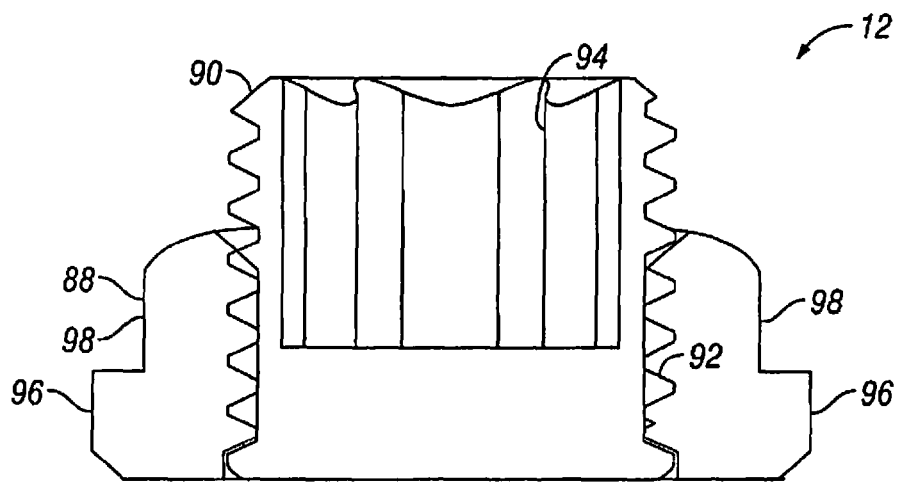
FIG. 11 is a cross-sectional view of a locking cap assembly in accordance with embodiments of the present invention.

Referring now to FIGS. 1 and 6-8, the tulip element 10 will be described in more detail in accordance with embodiments of the present invention. As illustrated, the tulip element 10 may comprise bore 62, a body 65 and arms 66 that extend upwardly from the body 65. In the illustrated embodiment, the arms 66 define a U-shaped channel 68 sized to receive the rod 14. Each of the arms 66 has an interior surface 70 the interior surface 70 having a threaded portion 72 for engaging corresponding threads on a screw-driving tool (e.g., tool 144 on FIGS. 27-29). The interior surface 70 of each of the arms 66 further may include a slot 74 for receiving corresponding tabs 96 (e.g., FIG. 9) of the locking cap assembly 12 and a recessed surface 76 for engaging corresponding protuberances 100 (e.g., FIG. 9) of the locking cap assembly 12. As illustrated, the recessed surface 76 of each of the arms 66 may be located above the slot 74. The interior surface 70 of each of the arms 66 further may include a protuberance 78. In the illustrated embodiment, the protuberance 78 of each of the arms 66 is located below the threaded portion 72 with the threaded portion 72 being located between the protuberance 78 and the slot 74. As best seen in FIG. 6, the interior surface 70 of each of the arms 66 further may form a downwardly facing seat 79, for example, which may limit or restrict movement of the locking clamp assembly 6 through the bore 62. Each of the arms 66 further may include an outer surface 80. The outer surface 80 of each of the arms 66 may include a tool engagement groove 82 formed on the outer surface 80 which may be used for holding the tulip element 10 with a suitable tool (not illustrated).

Figure 7:
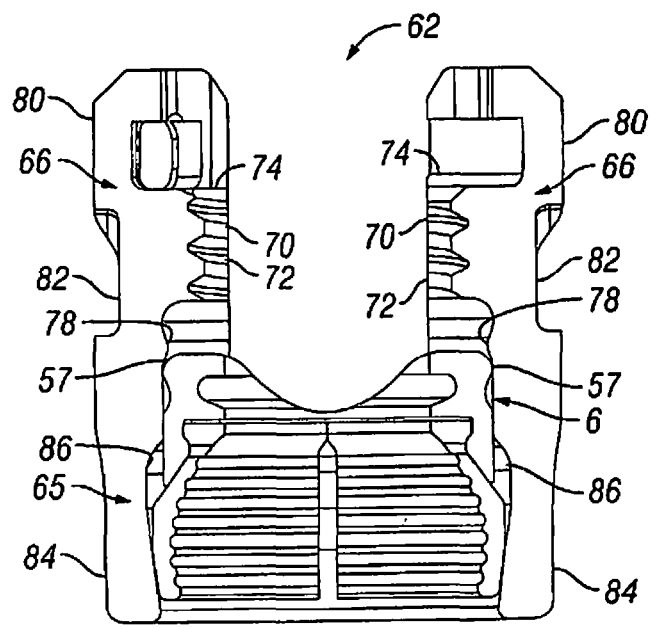
FIG. 7 is a cross-sectional view of a locking clamp assembly disposed in a tulip element in a locked configuration in accordance with embodiments of the present invention.

As illustrated, the body 65 of the tulip element 10 may have an outer surface 84, which may be curved or rounded, as best seen in FIG. 1. With particular reference to FIGS. 6 and 7, the body 65 further may include an inner wedge surface 86 disposed around a lower portion of the bore 62. In one embodiment, the inner wedge surface 86 forms a conical wedge. The inner wedge surface 86 of the body 65 of the tulip element 10, for example, may abut and engage the outer surfaces 30, 32 of the first and second clamp portions 26, 28 when the locking clamp assembly 6 is fully installed and locked in place.

In accordance with present embodiments, the locking clamp assembly 6 may be installed in the tulip element 10 in either an unlocked position or a locked position. FIG. 6 illustrates the locking clamp assembly 6 disposed in the tulip element 10 in the unlocked position in accordance with embodiments of the present invention. In FIG. 6, the locking clamp assembly 6 has been inserted into the tulip element 10 upwardly through the bore 62. The locking assembly 6 should be inserted until the upper lip 57 of the wedge element 8 passes the protuberances 78 located on the interior surfaces 70 of the arms 66 of the tulip element 10. The protuberances 78 should engage the upper lip 57 to secure the locking clamp assembly 6 in the tulip element 10. While not illustrated on FIG. 6, the bone fastener 4 (e.g., shown on FIG. 1) can now be placed into the locking assembly 6 through a snap fit with the clamp element 7. There should be sufficient clearance for the clamp element 7 to expand and snap around the head 16 of the bone fastener 4. The locking clamp assembly 6 and the tulip element 10, however, should still be free to rotate with respect to the bone fastener 4. The tulip element 10 can be moved and rotated to obtain a desired portion with respect to the bone fastener 4. The locking clamp assembly 6 should also move with the tulip element during rotation of the tulip element 10 with respect to the bone fastener 4. Once the tulip element 10 is at the desired position, the tulip element 10 may be locked onto the bone fastener 4. The locking clamp assembly 6 and the tulip element 10 should cooperate to lock the clamp assembly 6 onto the head 16 of the bone fastener 4.

FIG. 7 illustrates the locking clamp assembly 6 disposed in the tulip element 10 in the locked position in accordance with embodiments of the present invention. In FIG. 7, the locking clamp assembly 6 has been pushed downwardly in the bore 62 of the tulip element 10. As illustrated, the locking clamp assembly 6 has been pushed downward until the upper lip 57 of the wedge element 8 passes the protuberances 78 located on the interior surfaces 70 of the arms 66 of the tulip element 10. As the locking clamp assembly 6 moves downward, the clamp element 7 engages the body 65 of the tulip element 10. As illustrated, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4 (e.g., FIG. 1). In the locked position, tulip element 10 should be locked onto the bone fastener 4, thus preventing further positioning of the tulip element 10 with respect to the bone fastener 4.

Referring now to FIGS. 1 and 9-11, the locking cap assembly 12 will be described in more detail in accordance with embodiments of the present invention. As illustrated, the locking cap assembly 12 may comprise a body 88 and a set screw 90 threaded into a bore 92 in the body 88. The set screw 90 may have a length, for example, that is longer than the length of the bore 92. In the illustrated embodiment, at least a portion of the set screw 90 extends from the top of the body 88. In certain embodiments, the set screw 90 may have a tool engagement surface, for example, that can be engaged by a screw-driving tool or other device. The tool engagement surface can permit the physician to apply torsional or axial forces to the set screw 90 to advance the set screw 90 through the body 88 and onto the rod 14. When the locking cap assembly 12 is in its locked position, the set screw 90 can be advanced through the body 88 to engage the rod 14, applying downward force onto the rod 14 and securing it to the tulip element 12. In one embodiment, the set screw 90 forces the rod 14 downward and into contact with the locking clamp assembly 6 causing the locking cap assembly 6 to move downward in the tulip element 10. In the illustrated embodiment, the tool engagement surface of the set screw 90 is a polygonal recess 94. For instance, the polygonal recess 94 may be a hexagonal recess that receives a hexagonal tool, such as an allen wrench, for example. The present invention is intended to encompass tool engagement surfaces having other shapes, such as slot or cross that may be used, for example, with other types of screwdrivers. In an alternative embodiment (not illustrated), the engagement surface may be configured with a protruding engagement surface that may engage with a tool or device having a corresponding recess.

In accordance with present embodiments, the body 88 may have one or more projections. For example, the body 88 may comprise lower tabs 96 projecting radially from a lower end of the body 88. In the illustrated embodiment, the body 88 comprises a pair of lower tabs 96 located on opposite sides of the body 88. As illustrated, the lower tabs 96 may each have an outer surface 98 that is generally rounded in shape. In addition, while the body 88 is illustrated as having two lower tabs 96, the body 88 may comprise more than two lower tabs 96. As illustrated, the body 88 may further comprise protuberances 100. The protuberances 100 may engage with corresponding recessed surface 76 (e.g., FIG. 10) of the arms 66 of the tulip element 10. The protuberances 100 may be capable of providing a tactile or audible signal to the physician, such as a click that may be felt or heard, when the locking cap assembly 12 has reached its locking position. The protuberances 100 also may assist in maintaining the locking cap assembly 12 in its locked position. In the illustrated embodiment, the body 88 further may comprise tool engagement features. The tool engagement features may, for example, be used for holding or manipulating the locking cap assembly 12 with a suitable tool (not illustrated). In the illustrated embodiment, the locking cap assembly 12 includes upper tabs 102. As illustrated, the tabs 102 may be formed at the upper surface of the body 88. In the illustrated embodiment, the locking cap assembly 12 includes four upper tabs 102 at the corners of the upper surface. In addition, while the body 88 is illustrated as having four upper tabs 102, the body 88 may comprise more or less than four upper tabs 102.

To place the locking cap assembly 12 onto the tulip element 10, the lower tabs 96 should be aligned with the u-shaped channel 68 formed by the arms 66 of tulip element 10 and the locking cap assembly 12 can then be lowered downward into the bore 62 in the tulip element 10. Once the lower tabs 96 are aligned with the corresponding slots 74 in the arms 66 of the tulip element 10, the locking cap assembly 12 can be rotated. The slots 74 allow the lower tabs 96 to pass through the arms 66 when the lower tabs 96 and the slots 74 are aligned. The length of the slots 74 generally correspond to the amount of rotation needed to move the locking cap assembly 12 into or out of a locked position. In one embodiment, the locking cap assembly 12 rotates from about 60° to about 120° for placement into a locking positions, alternatively, about 80° to about 100°, and, alternatively, about 90°. As previously mentioned, the protuberances 100 can be configured to provide a tactile or audible signal to the physician when the locking cap assembly 12 has reached its locked assembly. In addition, the protuberances 100 can also assist in maintaining the locking cap assembly 12 in its locked position. Other features such as undercuts and geometric mating surfaces may be used to prevent rotation in the opposite direction. With the locking cap assembly 12 locked in place, the set screw 94 can then be rotated. As the set screw 94 moves downward and extends from the bottom of the base 88 of the locking cap assembly 12, the set screw 94 presses against the rod 14 securing it in the tulip element 10. In addition, the rod 14 may also be pressed downward into engagement with the locking clamp assembly 6 forcing it downward in the tulip element 10. As the locking clamp assembly 6 moves downward, the clamp element 7 engages the body 65 of the tulip element 10. As best seen in FIG. 7, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4 and secure it with respect to the tulip element 10.

Referring now to FIGS. 12-14, locking of the tulip element 10 onto the bone fastener 4 is illustrated in more detail in accordance with embodiments of the present invention. For the purposes of this illustration, the locking cap element 12 (e.g., FIG. 1) is not shown. The tulip element 10 shown in FIGS. 12-14 is similar to the tulip element 10 described previously except that the tulip element 10 does not include a threaded portion 72 (e.g., FIGS. 6-7) or a downwardly facing seat 79 (e.g., FIG. 6) in the interior surface 70 of the arms 66 of the tulip element 10. FIG. 12 illustrates the locking clamp assembly 6 installed in the tulip element 10 in an unlocked position. As previously mentioned, the locking clamp assembly 6 can be inserted into the tulip element 10 upwardly through the bore 62. As shown in FIG. 12, the locking assembly 6 should be inserted until the upper lip 57 of the wedge element 8 passes the protuberances 78 located on the interior surfaces 70 of the tulip element 10. The protuberances 78 should engage the upper lip 57 to secure the locking clamp assembly 6 in the tulip element 10. As illustrated by FIG. 13, the bone fastener 4 can now be placed into the locking assembly 6 through a snap fit with the clamp element 7. There should be sufficient clearance for the clamp element 7 to expand and snap around the head 16 of the bone fastener 4. The locking clamp assembly 6 and the tulip element 10, however, should still be free to rotate with respect to the bone fastener 4. The tulip element 10 can be moved and rotated to obtain a desired portion with respect to the bone fastener 4. Once the tulip element 10 is at the desired position, the tulip element 10 may be locked onto the bone fastener 4. The locking clamp assembly 6 and the tulip element 10 should cooperate to lock the clamp assembly 6 onto the head 16 of the bone fastener 4.

FIG. 14 illustrates the locking clamp assembly 6 disposed in the tulip element 10 in the locked position and clamping onto the bone fastener 4 to secure the bone fastener 4 with respect to the tulip element 10 in accordance with embodiments of the present invention. As seen in FIG. 14, the locking clamp assembly 6 has been pushed downwardly in the bore 62 of the tulip element 10 until the upper lip 57 of the wedge element 8 passes the protuberances 78 located on the interior surfaces 70 of the arms 66 of the tulip element 10. As the locking clamp assembly 6 moves downward, the clamp element 7 engages the body 65 of the tulip element 10 such that the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4. In the locked position, tulip element 10 should be locked onto the bone fastener 4, thus preventing further positioning of the tulip element 10 with respect to the bone fastener 4.

Figure 15:
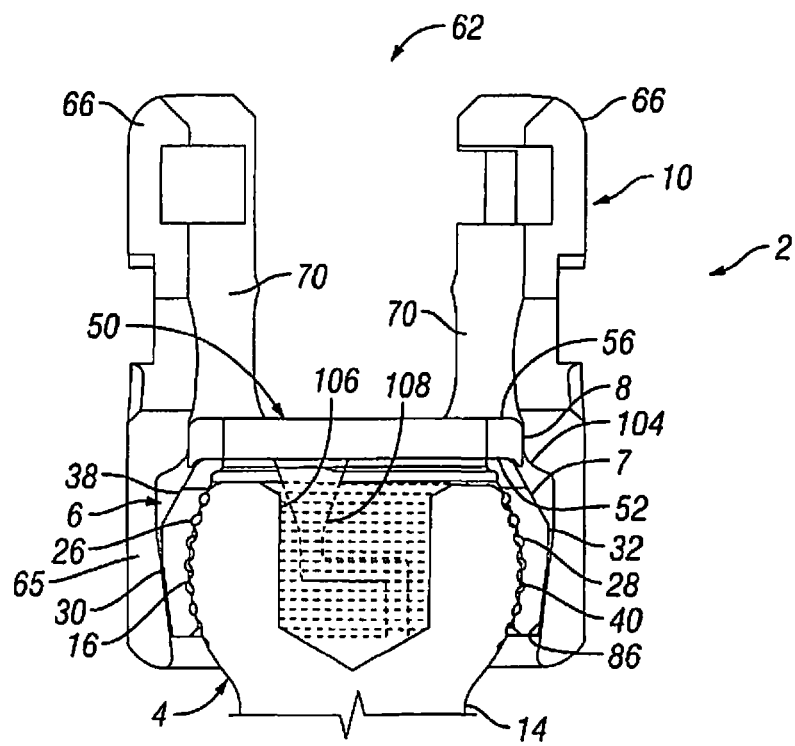
FIGS. 15-16 illustrate another alternative orthopedic fixation device in accordance with embodiments of the present invention.
Figure 16:
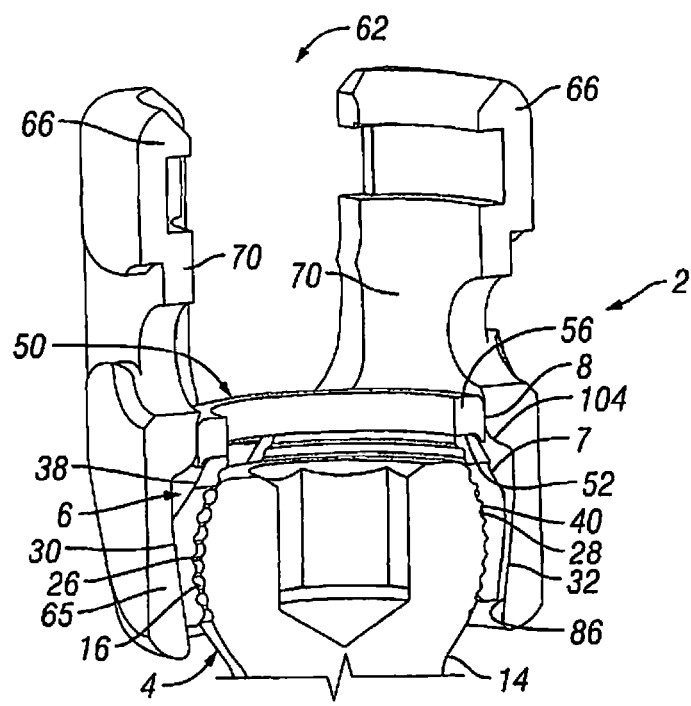

Referring now to FIGS. 15 and 16, an orthopedic fixation device 2 is described in accordance with alternative embodiments of the present invention. As illustrated, the orthopedic fixation device 2 comprises a bone fastener 4, locking clamp assembly 6, and a tulip element 10. For the purposes of this illustration, the locking cap assembly 12 (e.g., FIG. 1) is not shown. As previously mentioned, the locking clamp assembly 6 comprises a clamp element 7 and a wedge element 8. As illustrated, the clamp element 7 may include a first clamp portion 26 and a second clamp portion 28. In the illustrated embodiment, the first and second clamp portions 26, 28 each include an inner tapered surface 106, 108 such that the lower portions of the first and second clamp portions 26, 28 can expand when pressure is applied that constricts the upper portion of the first and second clamp portions 26, 28. In contrast, to the wedge element 8 that was previously described, embodiments of the upper surface 56 of the wedge element 8 illustrated on FIGS. 15 and 16 do not define a seat that receives the rod 14 (e.g., FIG. 1), but rather are generally planar with bore 50 penetrating there through. As illustrated, the wedge element 8 further includes an inner wedge surface 58 formed around a lower portion of the bore 50. As also previously mentioned, the tulip element 10 generally may comprise a bore 62, base 64, and arms 66. The inner diameter of the bore 62 in the upper portion of the tulip element 10 may be made smaller than either the combined size of the clamp element 7 and the bone fastener 4 or the diameter of the shaft 14 of the bone fastener 4, whichever is larger. As illustrated, the arms 66 may each comprise an interior surface 70. In the illustrated embodiment, the interior surface 70 includes inner tapered surface 104 rather than a downwardly facing seat 79 (e.g., FIG. 6) in the interior surface 70 of the arms 66 of the tulip element 10.

With continued reference to FIGS. 15 and 16, locking of the tulip element 10 onto the bone fastener 4 will be described in more detail in accordance with embodiments of the present invention. The first and second clamp portions 26, 28 of the clamp element 7 may be inserted one after another upwardly into the bore 62 of the tulip element 10. The first and second clamp portions 26, 28 may be pushed axially towards the top of the tulip element 10. The first and second clamp portions 26, 28 should continue to move upwardly until they engage the inner tapered surface 104 of the tulip element 10. Due the taper angle of the inner tapered surface 104, the upper portion of the first and second clamp portions 26, 28 will be forced to move inwards until the inner tapered surfaces 106, 108 of each of the first and second clamp portions 26, 28 come into contact. This contraction at the top of the first and second clamp portions 26, 28 should result in a wider opening at the bottom of the clamp element 7. The bone fastener 4 can then be inserted through the bottom of the bore 62 of the tulip element 10 and into the clamp element 7. The bone fastener 4 can then be manipulated, for example, to center the clamp element 7 into the head 16 of the bone fastener 4. The tulip element 10, however, should still be free to rotate with respect to the bone fastener 4. The tulip element 10 can be moved and rotated to obtain a desired portion with respect to the bone fastener 4. Once the tulip element 10 is at the desired position, the tulip element 10 may be locked onto the bone fastener 4.

To lock the tulip element 10, the bone fastener 4 can be pulled downward and because the clamp element 7 is in engagement with the bone fastener 4, the clamp element 7 should also move downward in the tulip element 10 such that the clamp element 7 engages the body 65 of the tulip element 10. As illustrated, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to clamp onto the head 16 of the bone fastener 4. The wedge element 8 can then be introduced downwardly from the top of the bore 62 in the tulip element 10 to seat on top of the clamp element 7. The wedge element 8 should engage the interior surfaces 70 of the tulip element 10 preventing upward movement of the clamp element 7, locking the clamp element 7 in its engagement with the head 16 of the bone fastener. In the locked position, the tulip element 10 should be locked onto the bone fastener 4, thus preventing further positioning of the tulip element 10 with respect to the bone fastener 4.

Figure 17:
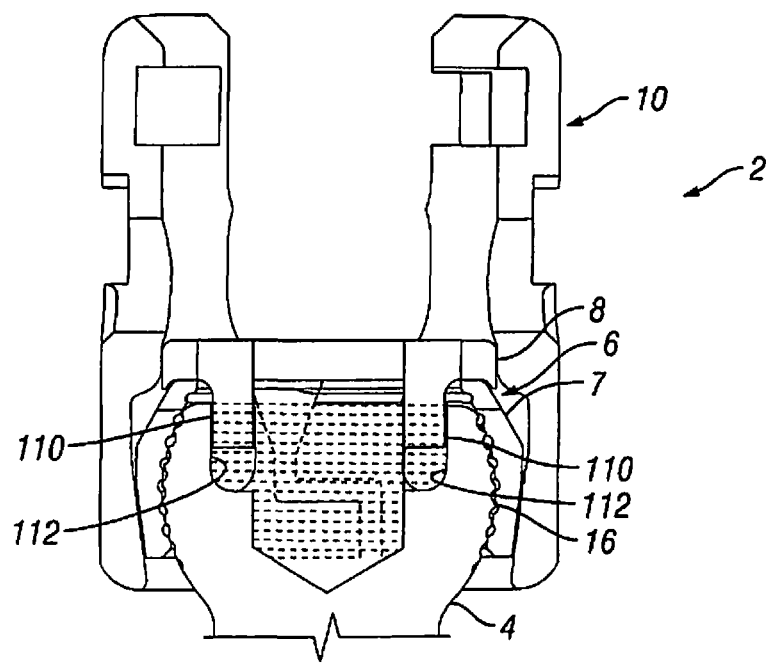
FIGS. 17-19 illustrate yet another alternative orthopedic fixation device in accordance with embodiments of the present invention.
Figure 18:
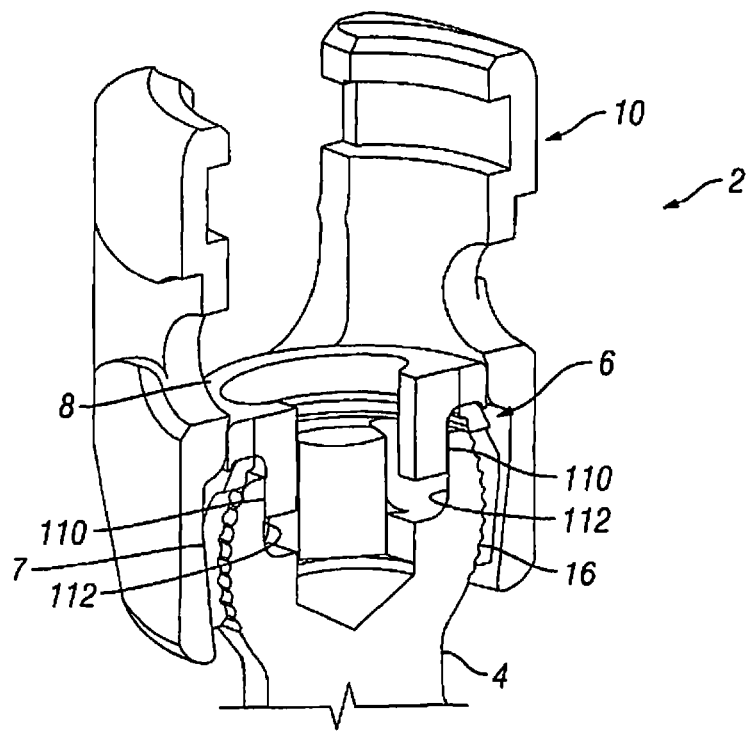
Figure 19:
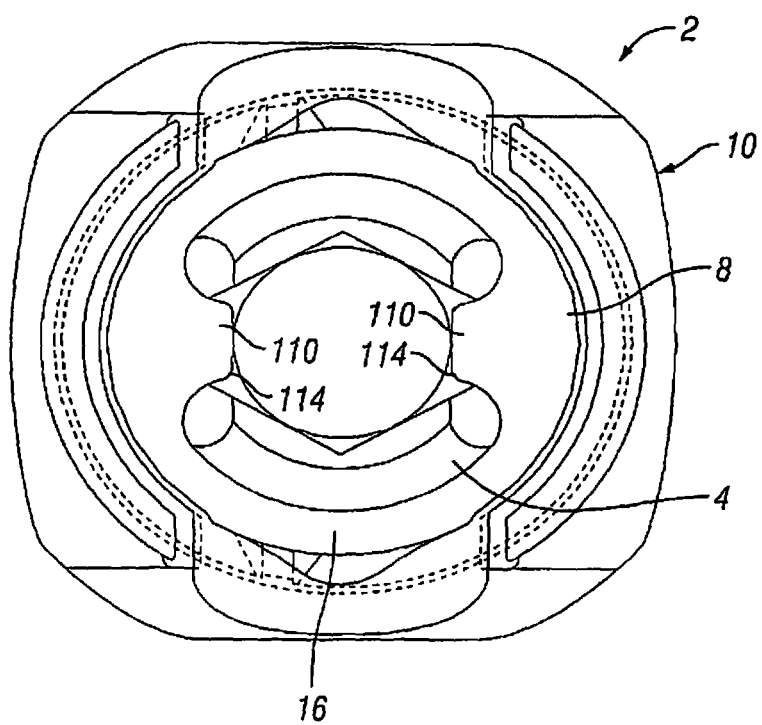

Referring now to FIGS. 17-19, an orthopedic fixation device 2 is described in accordance with alternative embodiments of the present invention. As illustrated, the orthopedic fixation device 2 comprises a bone fastener 4, a locking clamp assembly 6, and a tulip element 10. For the purposes of this illustration, the locking cap assembly 12 (e.g., FIG. 1) is not shown. In the illustrated embodiment, the locking clamp assembly 6 comprises a clamp element 7 and a wedge element 8. The orthopedic fixation device 2 is similar to the embodiments of FIGS. 15-16 except that embodiments of the wedge element 8 include downwardly extending tabs 110 that fits into corresponding slots 112 in the top of the head 16 of the bone fastener 4. In general, the tabs 110 should impart a uni-planar restraint on the bone fastener 4 so that it only slides along mating surfaces. The interior surfaces 114 of the tabs 110, best seen in FIG. 19, should forms the sides of the internal driving features. In an alternative embodiment (not illustrated), the wedge element 8 can be configured so that the tabs 110 are interconnected, for example, to impart more strength to the design of the wedge element 8.

Figure 21:
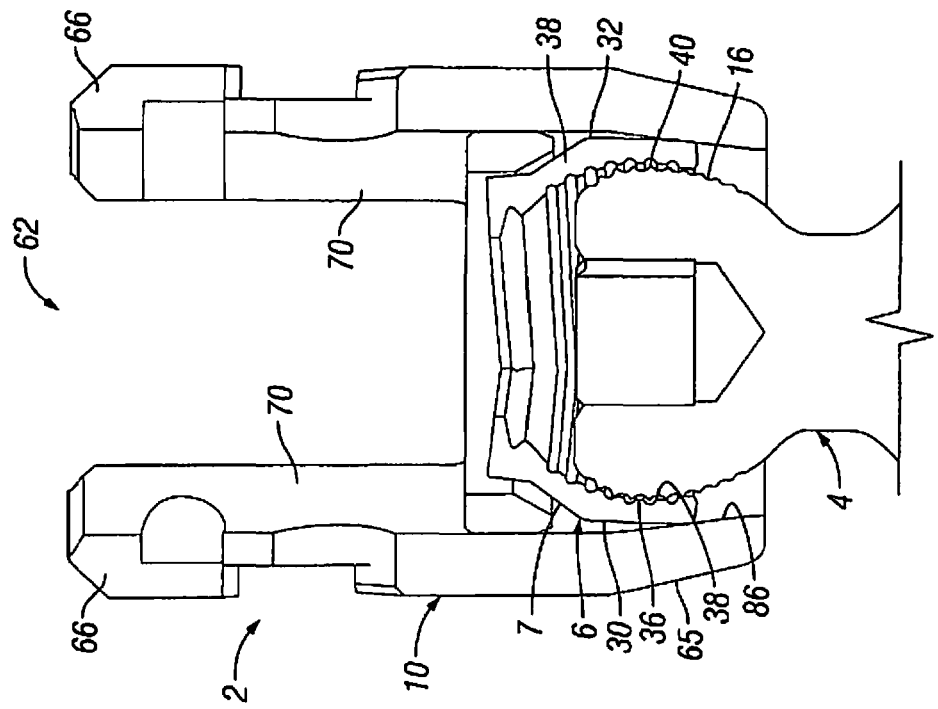
FIGS. 20-22 illustrate yet another alternative orthopedic fixation device in accordance with embodiments of the present invention.
Figure 20:
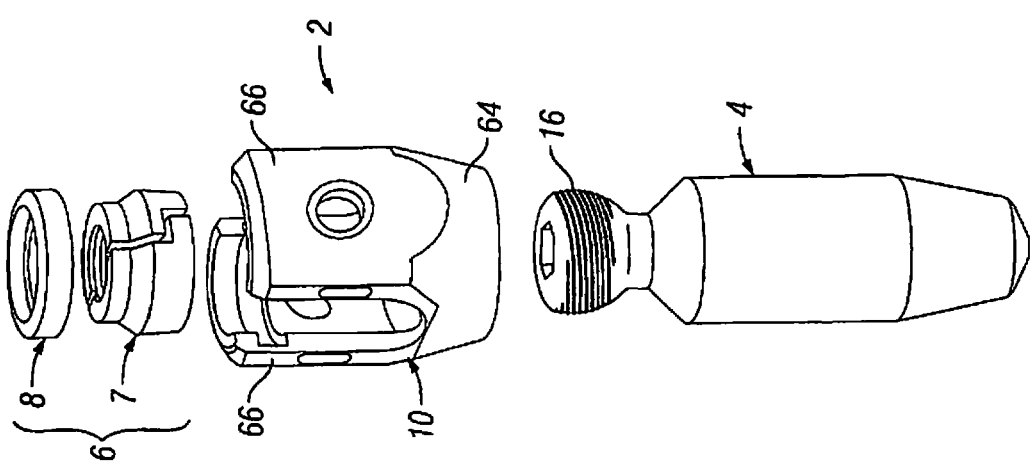

Referring now to FIGS. 20-21, an orthopedic fixation device 2 is described in accordance with alternative embodiments of the present invention. As illustrated, the orthopedic fixation device 2 comprises a bone fastener 4, a locking clamp assembly 6, and a tulip element 10. For the purposes of this illustration, the locking cap assembly 12 (e.g., FIG. 1) is not shown. In the illustrated embodiment, the locking clamp assembly 6 comprises a clamp element 7 and a wedge element 8.

The orthopedic fixation device 2 is similar to the embodiments of FIGS. 15-16 except that embodiments of the clamp element 7 are configured for top loading from the top of the bore 62 in the tulip element 10. Instead of being inserted upwardly from the bottom of the bore 62, the first and second clamp portions 26, 28 of the clamp element 7 are inserted downwardly from the top of the bore 62, until the clamp portions 26, 28 engage the inner wedge surface 86 of the body 65 of the tulip element 10. The bone fastener 4 can then be inserted upwardly from the bottom of the bore 62 of the tulip element 10 and into engagement with the clamp element 7 whereby the clamp element 7 will be pushed upwardly towards the top of the tulip element 10. The clamp element 7 will move higher until they engage an external temporary stop (not illustrated) that prevents further upward movement. As the clamp element 7 moves higher in the tulip element 10, the clamp portions 26, 28 adjust and reorient due to increased clearance with the inner wedge surface 86 of the tulip element 10 such that the opening at the bottom of the clamp element 7 is larger than the diameter of the head 16 of the bone fastener 4.

To lock the tulip element 10, the bone fastener 4 can be pulled downward and because the clamp element 7 is in engagement with the bone fastener 4, the clamp element should also move downward in the tulip element 10 such that the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to clamp onto the head 16 of the bone fastener 4. In accordance with present embodiments, the smallest inner diameter for the bore 62 in the tulip element 10 is smaller than the combined size of the clamp element 7 and the head 16 of the bone fastener 4, when in engagement. The wedge element 8 can then be introduced downwardly from the top of the bore 62 in the tulip element 10 to seat on top of the clamp element 7. The wedge element 8 should engage the interior surfaces 70 of the tulip element 10 preventing upward movement of the clamp element 7, locking the clamp element 7 in its engagement with the head 16 of the bone fastener. In the locked position, the tulip element 10 should be locked onto the bone fastener 4, thus preventing further positioning of the tulip element 10 with respect to the bone fastener 4.

Figure 22:
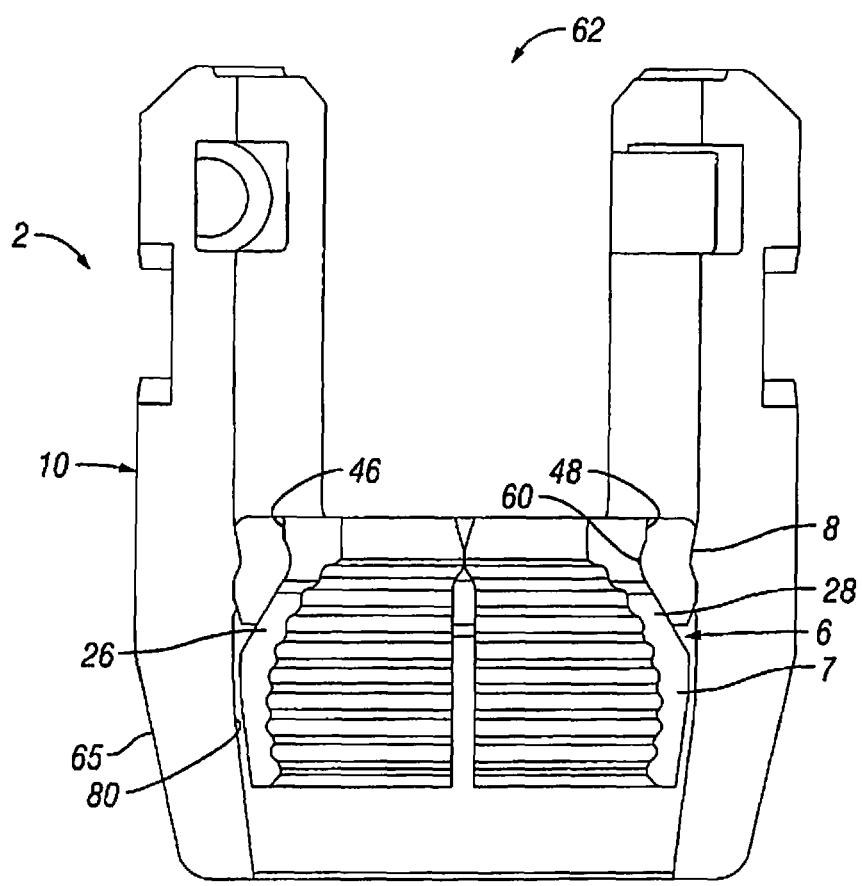

Referring now to FIG. 22, an orthopedic fixation device 2 is described in accordance with alternative embodiments of the present invention. As illustrated, the orthopedic fixation device 2 comprises a locking clamp assembly 6 and a tulip element 10. For the purposes of this illustration, the bone fastener (e.g., FIG. 1) and locking cap assembly 12 (e.g., FIG. 1) are not shown. In the illustrated embodiment, the locking clamp assembly 6 comprises a clamp element 7 and a wedge element 8.

The orthopedic fixation device 2 is similar to the embodiments of FIGS. 20-21 except that embodiments of the wedge element 8 include a retention feature for coupling with the clamp element 7. As illustrated, the wedge element 8 includes an inner protruding surface 60 that engages with the external lips 46, 48 of the first and second clamp portions 26, 28 of the clamp element 7 to secure the clamp element 7 in the wedge element 8. The locking clamp assembly 6 with the clamp element 7 secured in the wedge element 8 can then be inserted downwardly from the top of the bore 62 in the tulip element 10, until the clamp portions 26, 28 engage the inner wedge surface 86 of the body 65 of the tulip element 10. Once the bone fastener 4 is snapped into the clamp element 7, the locking clamp assembly 6 can be forced downwards through the tulip element 10 into its locked position to secure the bone fastener (e.g., FIG. 1) in the clamp element 7. In the locked position, the tulip element 10 should be locked onto the bone fastener 4, thus preventing further positioning of the tulip element 10 with respect to the bone fastener 4.

Figure 23:
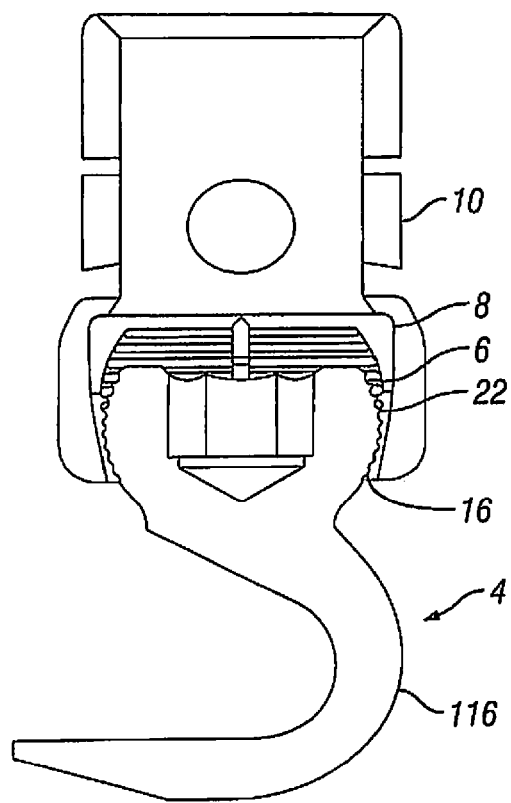
FIG. 23 illustrates an orthopedic fixation device comprising a bone hook in accordance embodiments of the present invention.

While the embodiments that are described and illustrated above generally illustrate a bone fastener 4 in shape of a screw having a head 16 and shaft 18 extending there from, it should be understood that other bone fasteners may also be used such as hooks and sacral blocks. Thus, the present invention may be used with a wide variety of bone fasteners in addition to a bone screw, as described above. For example, FIG. 23 illustrates an embodiment in which the bone fastener 14 includes a head 16 having an extension in the form of a hook 116 that extends from the head 16. In the illustrated embodiment, the head 16 is secured in the tulip element 10 by the clamp element 7 and the wedge element 8. As illustrated, the head 16 may have a roughened or textured surface 22 that improves engagement with the clamp element 7.

Figure 24:
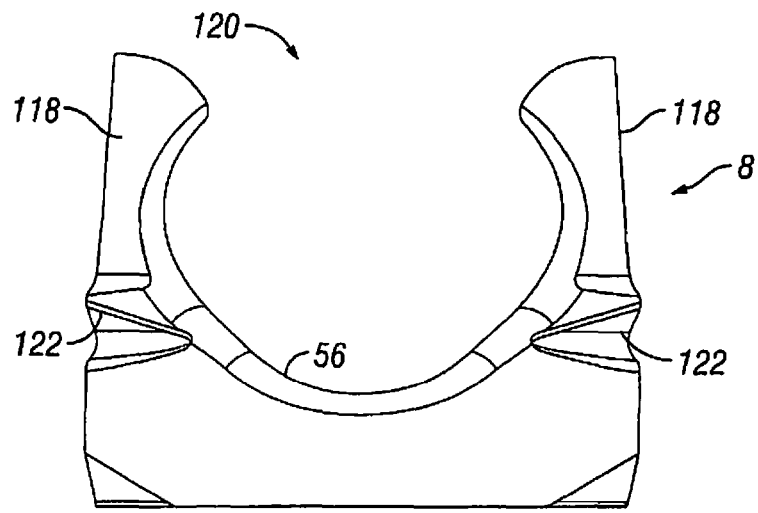
FIGS. 24-25 illustrate an alternative wedge element in accordance with embodiments of the present invention.
Figure 25:
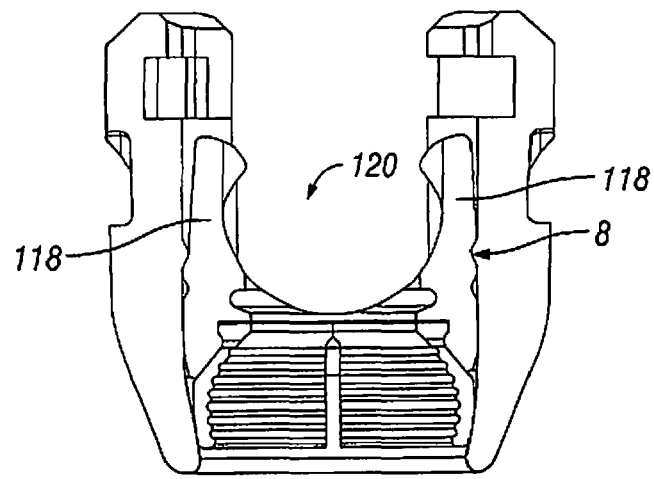

FIGS. 24 and 25 illustrate a wedge element 8 having an optional rod retention feature, in accordance with embodiments of the present invention. In some embodiments, the rod retention feature of the wedge element 8 may be added to enhance retainment of the rod 14 (e.g., FIG. 1) in a surgical procedure. In the illustrated embodiment, the rod retention feature is in the form of seat extensions 118 that will cradle the rod 14 to retain it in the wedge element 8. As illustrated, the wedge element 8 comprises an upper surface 56 defining a seat for receiving the rod 14. The wedge element 8 further may comprise seat extensions 118 for retaining the rod in the wedge element 8. In one embodiment, the seat extensions 118 may be configured to flex when a rod 14 is pushed down through opening 122 at the top of the seat extensions 118. When pressed down, the rod 14 may engage the ends of the seat extensions 118 causing the seat extensions 118 to flex outward increasing the size of the opening so that the rod 14 can be moved downwards to rest on the upper surface 56 of the wedge element 8. In other words, the rod 14 may be snapped past the seat extensions 118 in accordance with some embodiments. In the illustrated embodiment, the wedge element 8 further includes notches 122 to facilitate flexing of the seat extensions 118.

While the embodiments that are described and illustrated above generally illustrate a tulip element 10 in the general shape of a "U" for coupling the rod 14 to the bone fastener 4, it should be understood that any of a variety of different coupling elements may be used in accordance with embodiments of the present invention. For example, the coupling element may be open (e.g., tulip element 10 on FIG. 1) or closed. In some embodiments, the rod 14 may be top loaded into an open coupling element. In other embodiments, the rod 14 may be side loaded, for example, into a closed coupling element. In some embodiments, the coupling element may be an open, closed, or offset iliac connector. In yet other embodiments, the coupling element may be a posted screw connector. In addition, the coupling element may be configured to move polyaxially, monoaxially, or uni-planar with respect to the bone fastener 4 prior to locking of the coupling element onto the bone fastener 4.

Figure 26:
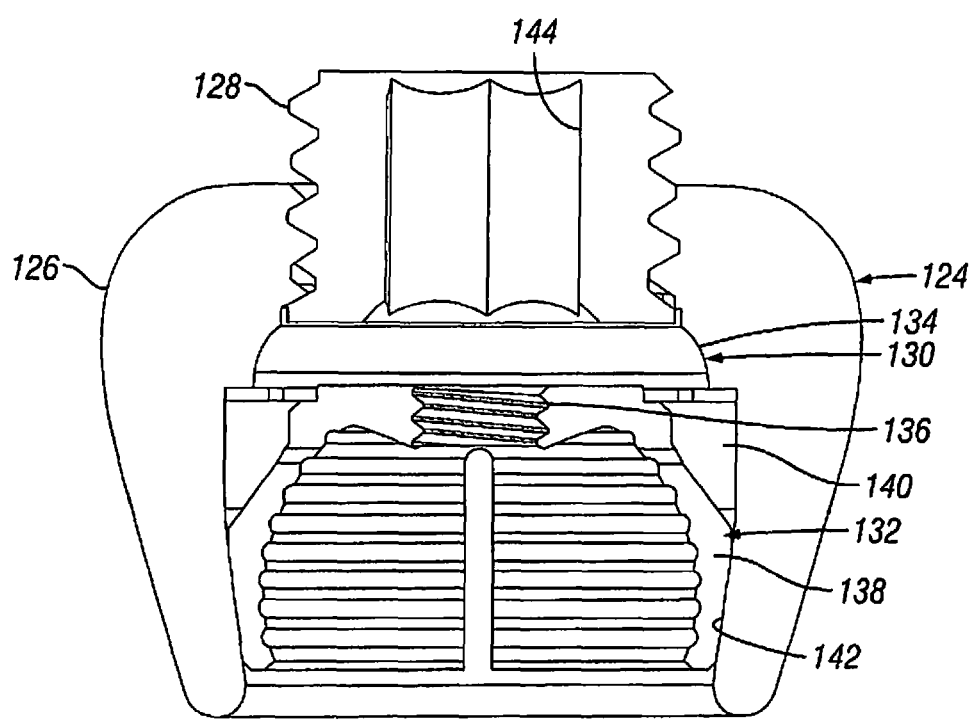
FIG. 26 illustrates an offset iliac connector in accordance with embodiments of the present invention.

FIG. 26 illustrates a coupling element in accordance with alternative embodiments of the present invention. In the illustrated embodiment, the coupling element is an offset iliac connector 124. The offset iliac connector 124 should allow, for example, iliac screw placement prior to selection of coupling element type. The design of the offset iliac connector 124 should also allow, for example, removal of the iliac connector 124 using a specialized instrument (not illustrated) to change the coupling element type in situ. As illustrated, the offset iliac connector 124 includes an offset housing 126, a set screw 128, a spring washer 130, and a locking clamp assembly 132. In accordance with embodiments of the present invention, the set screw 128 can be installed through the bottom of the offset housing 126 and rotated (e.g., counter clockwise) until tight. After installation of the set screw 128, the spring washer 130 may then be inserted upwardly through the bottom of the offset housing 126. In the illustrated embodiment, the spring washer 130 has a washer portion 134 and a spring portion 136 that extends down from the washer portion 134. The locking clamp assembly 132 may then be inserted upwardly through the bottom of the offset housing 126 and snapped into a place, in a manner similar to the previously described embodiments. In the illustrated embodiment, the locking clamp assembly 132 includes a wedge element 138 and a clamp element 140. To engage the offset connector with a head 16 of a bone fastener 4 (e.g., FIG. 1), the offset connector can be pushed down onto the head 16. The head 16 of the bone fastener 4 should be pushed upward into the locking clamp assembly 132. The bone fastener 4 should push the locking clamp assembly 132 upward into the spring portion 136 of the spring washer 130 until sufficient clearance is achieved between the locking clamp assembly 132 and the offset housing 126 for the bone fastener 4 to snap into the locking clamp assembly 132. The spring washer 130 should then provide downward force onto the locking clamp assembly 132 such that the interior wedge surface 142 of the offset housing 126 applies pressure to the locking clamp assembly 132 forcing the clamp element 138 to clamp onto the head 16 of the bone fastener 4. In some embodiments, a specialized instrument (not illustrate) can be threaded through the polygonal recess 144 (e.g., a hexagonal recess) in the set screw 128 and into the locking clamp assembly 132. The threading of the instrument should provide sufficient clearance with the offset housing 126 for removal of the offset iliac connector 124 from the bone fastener 4 without removal of the bone fastener 4 from the bone.

Figure 29:
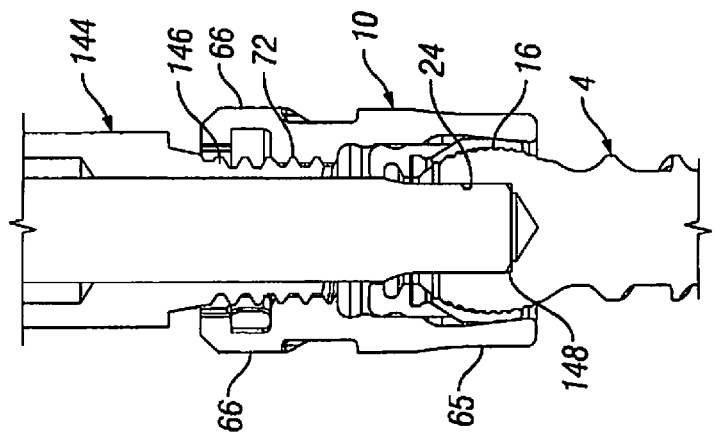
FIGS. 27-29 illustrate a bone fastener having a threaded instrument interface in accordance with embodiments of the present invention.
Figure 28:
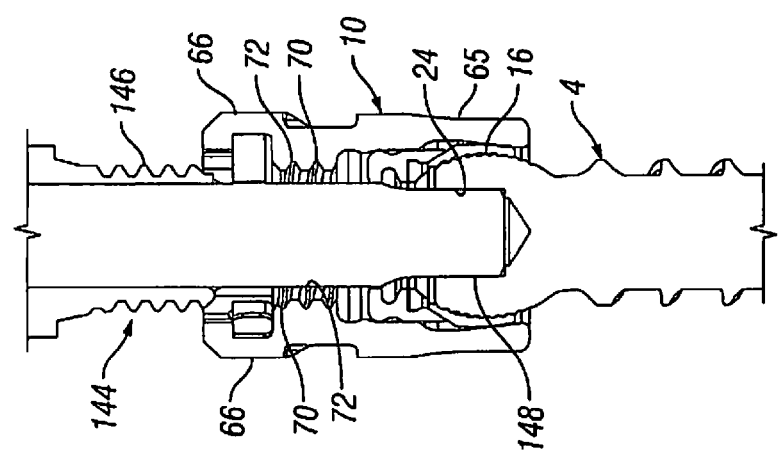
Figure 27:
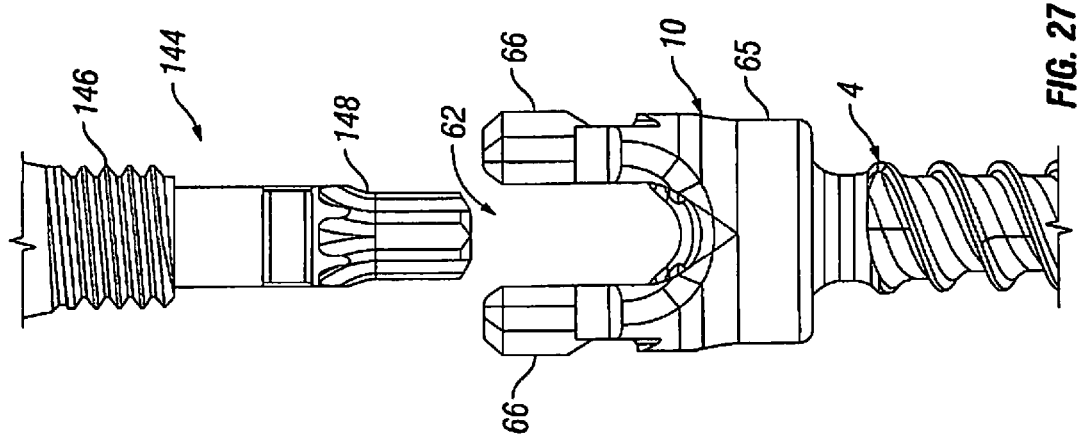

As previously illustrated and described with respect to FIG. 1, the tulip element 10 may include a threaded portion 72. FIGS. 27-29 illustrate the threaded portion 72 of the tulip element 10 in more detail. As illustrated, the tulip element 10 includes a body 65 and arms 66. As best seen in FIG. 28, the arms 66 each include an interior surface 70 having a threaded portion 72. In accordance with present embodiments, a bone fastener 4 can be secured to the tulip element 10. As illustrated, a tool 144, which may be, for example, a screw-driving tool, can be placed through the bore 62 in the tulip element 10 and into engagement with the tulip element 10 and the bone fastener 4. In the illustrated embodiment, the tool 144 includes a threaded portion 146 that engages the threaded portion 72 of the tulip element 10. The tool 144 further includes an engagement end 148 below the threaded portion 72 that engages with the polygonal recess 24 (e.g., hexagonal) in the head 16 of the bone fastener 4. In this manner, a rigid connection may be formed between the bone fastener 4 and the tool 144.

Figure 30:
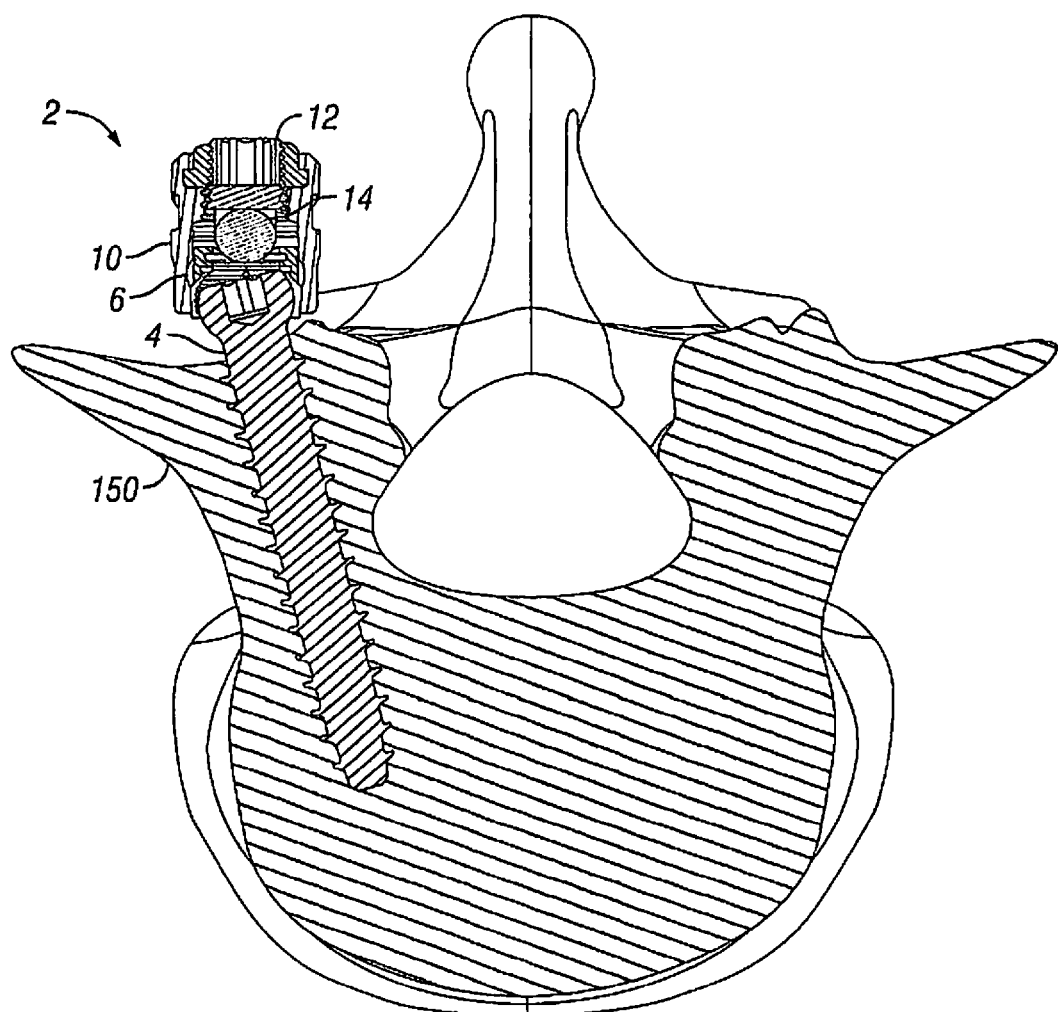
FIG. 30 illustrates a cross-sectional view of a vertebra having an orthopedic fixation device installed therein in accordance with embodiments of the present invention.

FIG. 30 illustrates installation of the orthopedic fixation device 2 in a vertebra 150 in accordance with embodiments of the present invention. As illustrated, the bone fastener 4 may be implanted into the vertebra 150. The bone fastener 4 may then be secured to the tulip element 10 using, for example, the locking clamp assembly 6. The tulip element 10 can then be moved and rotated into a desired position with respect to the bone fastener 4 and then locked onto the bone fastener 4. In one embodiment, the tulip element 10 is fixed onto the bone fastener 4 contemporaneously with securing the rod 14 to the tulip element 10 with the locking cap assembly 12. In this manner, the rod 14 can be secured in a fixed position relative to the vertebra 150.

Additional embodiments of a locking clamp assembly and individual features are shown in FIGS. 31-39. In these figures, the locking clamp assembly is a uniplanar locking clamp assembly, whereby a screw in the uniplanar locking clamp assembly is capable of uniplanar motion.

In some surgeries, it may be desired to use more than one type of screw, such as a polyaxial screw and/or a uniplanar screw. In some cases, a surgeon may initially choose to use a certain type of screw, and then change course during surgery and alter the type of screw to be used. For systems that use polyaxial screws or uniplanar screws with fixed, unremovable tulip heads, this may require removing a screw completely from a bone before replacing it with another screw. To solve these difficulties, the system described herein advantageously utilizes modular tulip assemblies that are loaded on top of a screw, or in other words, accommodate bottom-loaded screws. These modular tulip assemblies can accommodate polyaxial motion or uniplanar motion between the tulip assemblies and the screw, and can simply be exchanged during the course of a surgery. Accordingly, when a surgeon desires to replace one type of screw for another (e.g., polyaxial for uniplanar or vice versa), he can simply remove the modular tulip component and replace it with another, while leaving the screw in place (e.g., in a vertebral body).

Figure 31:
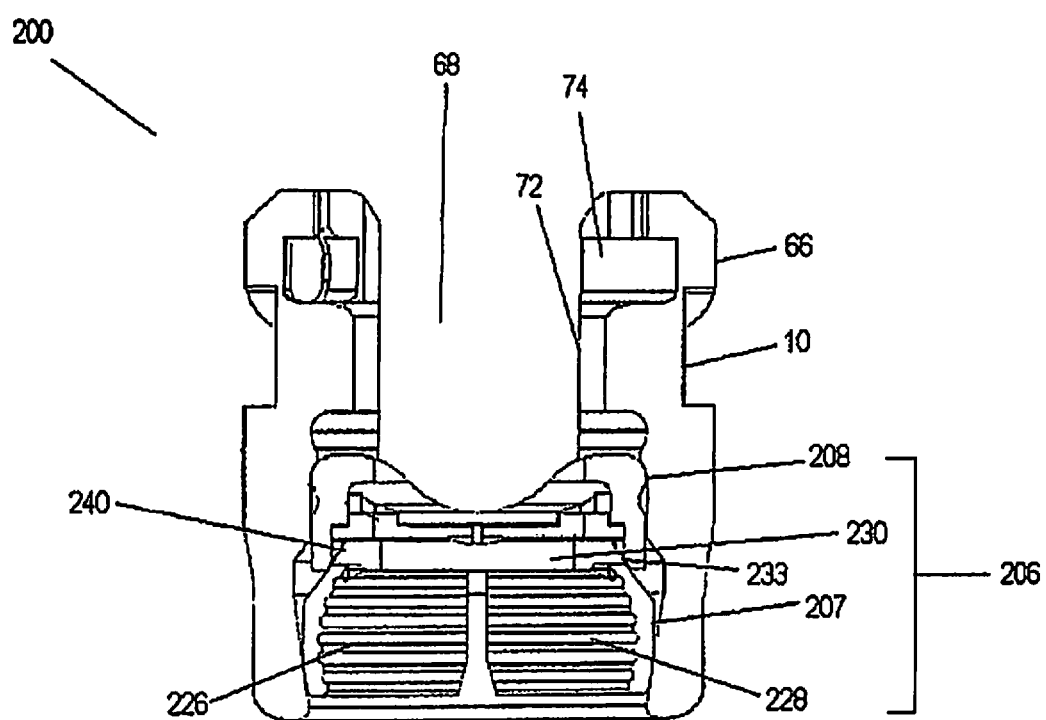
FIG. 31 illustrates a cross-sectional view of a uniplanar tulip assembly in accordance with embodiments of the present invention.

FIG. 31 illustrates a uniplanar tulip assembly that can be attached to the top of a bone fastener. Advantageously, the uniplanar tulip assembly 200 is a modular assembly that can be loaded onto a bone fastener 4, even when the bone fastener 4 is fixed in a bone member. The uniplanar tulip assembly 200 comprises similar elements to the assembly shown in FIG. 1, including a tulip element 10 and a locking clamp assembly 206 comprising a wedge element 208 and a clamp element 207. In addition to these components, the assembly 200 includes a ring member 230 that is fixed to the clamp element 207. This ring member 230 effectively restricts motion between the bone fastener 4 and the tulip element 10 to be uniplanar.

The tulip element 10 is similar to the tulip element in FIG. 1, and includes a pair of arms 66 that form a U-shaped channel for receiving a rod 14 therebetween. In some embodiments, the interior walls of the arms 66 include threaded portions 72 for engaging corresponding threads on a screw-driving tool. Each of the arms 66 also includes a slot 74 for receiving tabs of a locking cap assembly that can be placed on top of the rod 14.

Like the locking clamp assembly 6 in FIG. 1, the locking clamp assembly 206 also includes a wedge element 208 operably attached to a clamp element 207. The integrated wedge element 208 and clamp element 207 are capable of locking with the tulip element 10, similarly as described with respect to FIGS. 6 and 7.

The wedge element 208 comprises a bore therethrough that is sized to receive an upper portion of the clamp element 207. The top surface of the wedge element 208 is a curved saddle portion for seating a rod 14 therein.

The clamp element 207 is comprised of a first clamp portion 226 and a second clamp portion 228. Like the clamp element 7 discussed above, outer surfaces of the first and second clamp portions 226, 228 can slidingly engage an inner surface of the wedge element 208. The clamp element 207 can be inserted until lips of the first and second clamp portions 226, 228 pass an inner protruding surface of the wedge element 208. The inner protruding surface engages the external lips to secure the clamp element 207 in the wedge element 208, thereby integrating the wedge element and the clamp element.

The outer surfaces of the clamp element 207 can include at least one opening 240 for receiving a ring element (shown in FIG. 33A) therethrough. In some embodiments, the clamp element 207 includes two opposing openings 240 on opposite side walls. In some embodiments, each of the first and second clamp portions 226, 228 include an opening such that when the two portions are combined, a continuous opening 240 is formed on an outer surface of the clamp element 207.

A ring element 230 (shown in FIGS. 33A-33D) is configured to be received in the clamp element 207. The ring element 230 includes a pair of protrusions 233 that are each received in an opening in the clamp element 207. The protrusions 233 are configured to glide along the openings 240 of the clamp element 207, thereby allowing for motion along a plane of axis (e.g., axis A-A shown in FIG. 33C) between the pair of protrusions. In an orthogonal plane, the mating of the protrusions 233 with the openings 240 of the clamp element 207 prevents motion of the screw head in that plane, thereby restricting the motion to be uniplanar motion. Advantageously, in some embodiments, the addition of the ring element 230 to the tulip assembly can convert a modular polyaxial tulip assembly into a uniplanar tulip assembly. More details regarding the ring element 230 are discussed below with respect to FIGS. 33A-33D.

The uniplanar locking clamp assembly 206 is assembled as follows. The clamp element 207 is first assembled with the ring element 230, and then the wedge element 208, prior to assembly with the tulip element 10. The ring element 230 is inserted into the mating thru-cuts or openings 240 formed in the clamp element 207. The saddle or wedge element 208 is mated to the clamp element 207 through a snap-fit feature, creating a uniplanar locking assembly 206. The uniplanar locking assembly 206 can then be inserted into the tulip element 10, similarly to as discussed above with respect to FIGS. 6 and 7.

Figure 32:
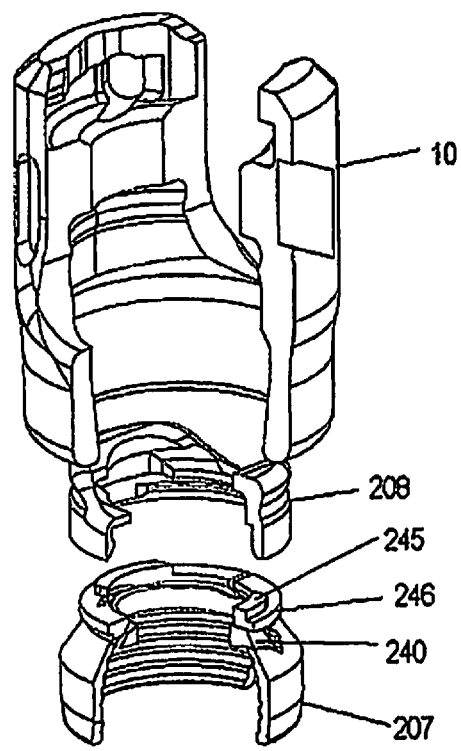
FIG. 32 illustrates a disassembled view of portions of the uniplanar tulip assembly in accordance with embodiments of the present invention.
Figure 33A:
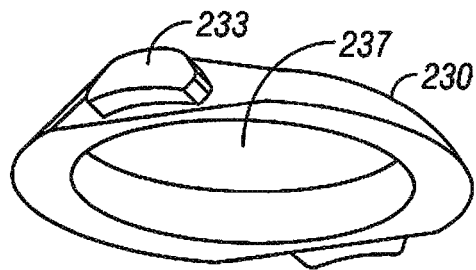
FIG. 33A illustrates a bottom perspective view of a uniplanar ring element in accordance with embodiments of the present invention.
Figure 33B:
FIG. 33B illustrates a side view of the uniplanar ring element of FIG. 33A.
Figure 33C:
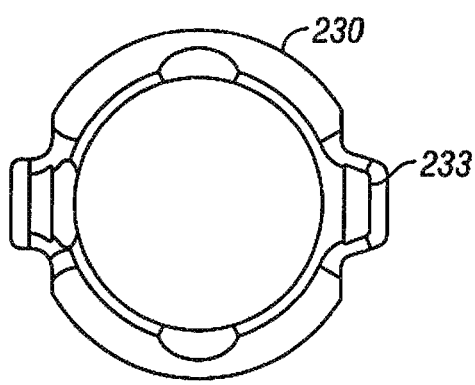
FIG. 33C illustrates a top view of the uniplanar ring element of FIG. 33A.
Figure 33D:
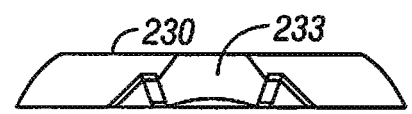
FIG. 33D illustrates another side view of the uniplanar ring element of FIG. 33A.

FIG. 32 illustrates a disassembled view of portions of the uniplanar tulip assembly in accordance with embodiments of the present invention. From this view, one can see the lips 246 of the clamp element 207 that are mateable with the saddled wedge element 208. In addition, from this view, one can see an upper surface of the clamp element 207, which includes a protruding feature 245. In some embodiments, each of the clamp portions 226 and 228 includes a protruding feature 245 that fits into a corresponding mating cut formed in the wedge element 208. The protruding features 245 advantageously maintain the orientation between the clamp element 207 and the wedge element 208. These features 245 keep the uniplanar locking clamp assembly 206 aligned throughout both assembly and use.

FIGS. 33A-33D illustrate different views of a ring element 230 with protrusions 233 according to some embodiments. The ring element 230 includes an internal opening 237 for receiving the head of a screw fastener 4. The head of the screw fastener 4 is capable of movement in the ring element 230; however, such movement is restricted to uniplanar movement due to the engagement between the ring element protrusions 233 and the openings 240 in the clamp element 207. In some embodiments, the protrusions 233 have curved upper and lower surfaces, such that the gliding motion of the ring element 230 in the openings 240 can be in an arc. In other embodiments, the protrusions 233 have flat upper and lower surfaces, such that the gliding motion of the ring element 230 in the openings 240 can be substantially straight. In addition, in some embodiments, the lowest surfaces of the protrusions 233 are raised slightly above the lowest surfaces of the base of the ring element 230.

Figure 34:
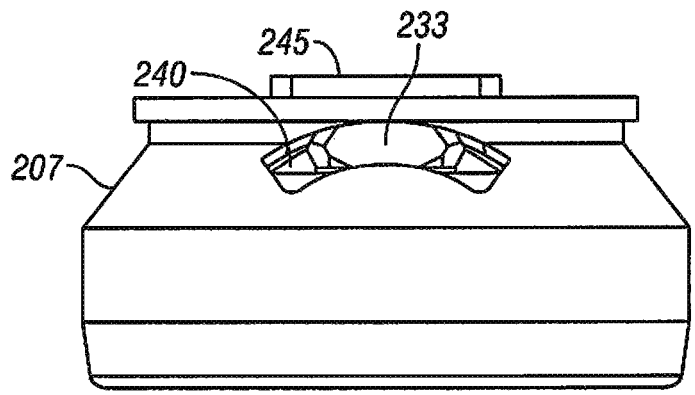
FIG. 34 illustrates a side view of a clamp element mated to a uniplanar ring element in accordance with embodiments of the present invention.

FIG. 34 illustrates a side view of the ring element 230 mated to the clamp element 207. From this view, one can see how the protrusions 233 of the ring element 230 are curved, and how the openings 240 in the clamp element 207 are also curved to provide for glided motion of the protrusions that is an arc.

Figure 35:
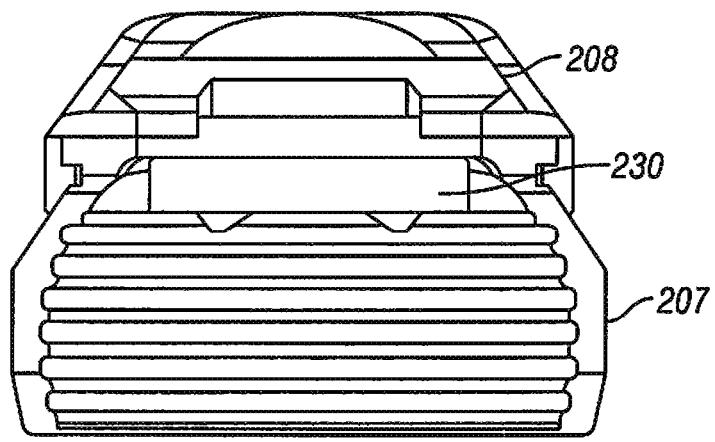
FIG. 35 illustrates a side view of a wedge element mated with a clamp element in accordance with embodiments of the present invention.

FIG. 35 illustrates a side view of the wedge element 208 mated with the clamp element 207. From this view, one can see how lips of the clamp element 207 mate with recesses of the wedge element 208 to secure the clamp element 207 (including a ring element 230) to the wedge element 208.

FIG. 36 illustrates an alternate side view of the wedge element 208 mated with the clamp element 207. From this view, one can see the protruding feature 245 that extends from an upper surface of the clamp element 207 to maintain a desired orientation and alignment between the clamp element 207 and the wedge element 208.

FIG. 37 illustrates a top perspective view of the wedge element 208 mated with the clamp element 207 with the ring element absent. From this view, one can see how the opening 240 for receiving a ring element protrusion is visible even when the wedge element 208 is mated with the clamp element 207.

FIG. 38 is a top view of a saddle or wedge element 208 for use in the uniplanar locking clamp assembly. The wedge element 208 is configured to include one or more cut-outs that can receive one or more protruding features 245 that extend from an upper surface of the clamp element 207, thereby maintaining a desired orientation and alignment between the clamp element 207 and the wedge element 208.

Figure 39A:
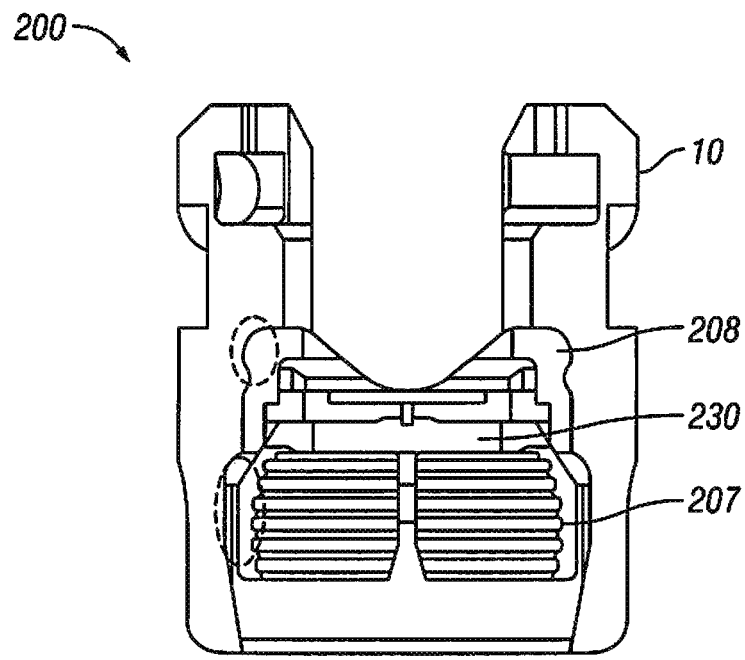
FIG. 39A illustrates a uniplanar tulip assembly in an unlocked position in accordance with embodiments of the present invention.
Figure 39B:
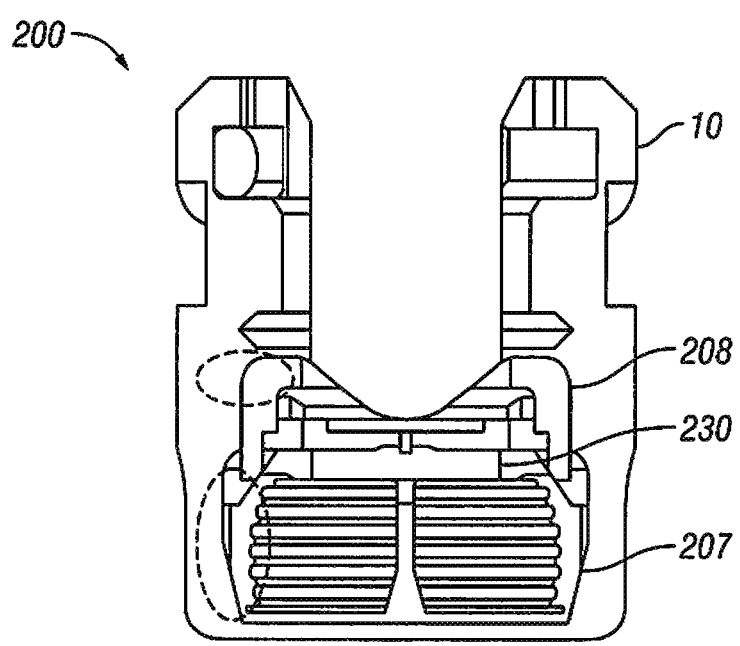
FIG. 39B illustrates the uniplanar tulip assembly of FIG. 38A in a locked position.

FIGS. 39A and 39B illustrate the uniplanar locking clamp assembly in an unlocked and a locked position, respectively. While the uniplanar locking clamp assembly 200 differs from the assembly in FIGS. 6 and 7, as it includes a tulip element 10, wedge element 208, clamp element 207 and the additional ring element 230, positioning the uniplanar locking assembly 200 in the unlocked and locked positions is performed similarly as discussed above. In some embodiments, the uniplanar locking clamp assembly 200 can be easily removed from a screw head during surgery, and can be replaced with a different type of modular clamp assembly. In some embodiments, to remove the uniplanar locking clamp assembly 200, a removal instrument can have a distal end that mates and lodges in revolve cuts/relief areas 77 (shown in FIG. 2). The removal instrument will cause the expansion of the wedge element and/or clamp element, while allows the entire locking assembly 200 to translate up or down, thereby locking or unlocking the tulip element to the screw head. Such a removal can be performed on any of the tulip elements, including the polyaxial and uniplanar elements, described above.

Figure 40:
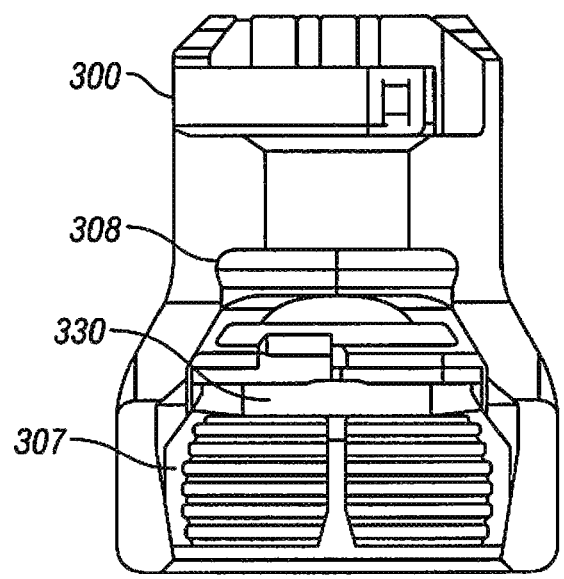
FIG. 40 illustrates a cross-sectional view of a fracture screw with uniplanar ring element in accordance with embodiments of the present invention.

FIG. 40 illustrates a cross-sectional view of a fracture screw assembly with a uniplanar ring element in accordance with some embodiments. The fracture screw assembly 300 can be used to provide controlled movement of one vertebrae in order to increase or decrease sagittal curves in the spine (e.g., kyphosis or lordosis). In some embodiments, the fracture screw assembly 300 is similar to the uniplanar screw assembly 200 described above, and includes a wedge element 308, a clamp element 307, and a ring element 330 therein; however, unlike the ring element 230 that restricts motion along the axis of the rod slots to be uniplanar motion, the ring element 330 restricts motion along an axis that is orthogonal to the rod slots. Each of the openings 340 in the clamp element 307 for receiving the ring element 330 are thus placed at approximately 90 degrees with respect to an opening in the clamp element 207 shown in previous embodiments.

Figure 41:
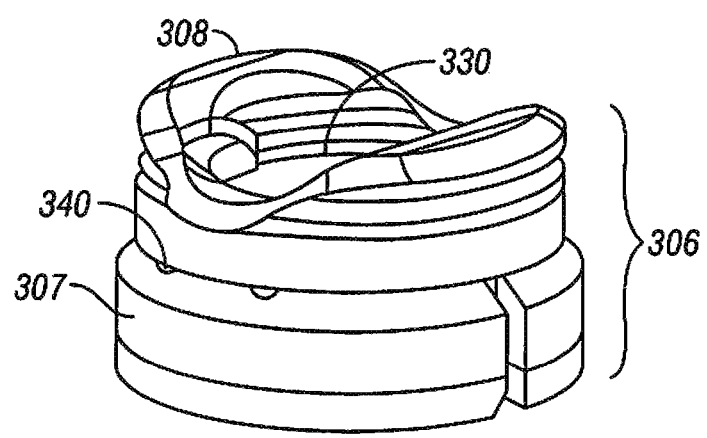
FIG. 41 illustrates a perspective view of a uniplanar locking assembly for the fracture screw of FIG. 40.

FIG. 41 illustrates a perspective view of a uniplanar locking assembly for the fracture screw of FIG. 40. From this view, one can see how the saddle or wedge element 308 substantially, or in some cases completely, covers the openings 340 in the clamp element 307 when the wedge element 308 and clamp element 307 are assembled.

In addition to the systems described above, a number of hook systems can be provided that are capable of receiving modular tulip assemblies that can accommodate polyaxial motion or uniplanar motion between the tulip assemblies and the hooks. Advantageously, a surgeon can decide which type of tulip assembly is desirable, and can modify or change one or more tulip assemblies in situ over the hook systems to assist in a particular surgery. In some embodiments, the hook systems can hook onto bone members. In other embodiments, the hook systems can hook onto rod members (e.g., of spinal stabilization systems) and serve as cross-connectors.

Figure 42A:
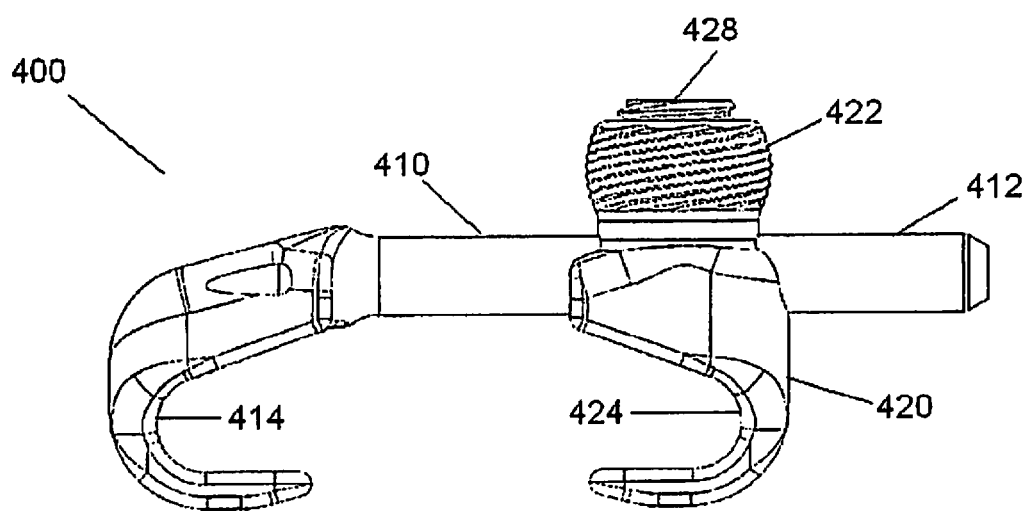
FIGS. 42A-42C illustrate different views of a hook system in accordance with embodiments of the present application.
Figure 42B:
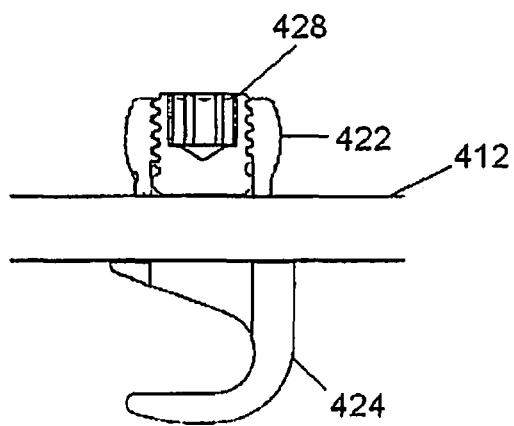
Figure 42C:
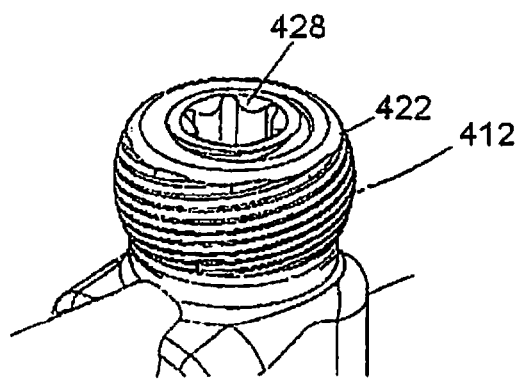

FIGS. 42A-42C illustrate different views of a hook system in accordance with embodiments of the present application. The hook system 400 comprises a male hook component 410 and a female hook component 420. The male hook component 410 is comprised of a rod member 412 and a hook member 414. The female hook component 420 is comprised of a head member 422 and a hook member 424.

The male hook component 410 is configured to grip onto a bone member via its hook member 414. The female hook component 420 is configured to slide along the rod member 412 of the male hook component 410. Advantageously, the female hook component 420 is capable of both translational and rotational adjustment until it is locked into position via locking member 428. In some embodiments, the locking member 428 comprises a set screw that is locked via rotation by an instrument, such as a screw driver. As shown in FIG. 2, rotation of the set screw 428 causes the set screw to translate downwardly and compress on the rod member 412 of the male hook component 410. In some embodiments, like the male hook component 410, the female hook component 420 also includes a hook member 424 that is capable of gripping onto a bone member.

In some embodiments, the head member 422 of the female hook component 420 is configured to receive a modular tulip assembly, as shown for example in FIG. 2. In some embodiments, the head member 422 can be a rounded member having surface texturing thereon. Advantageously, the head member 422 of the female hook component 420 matches the head of one or more fasteners used in a surgery (e.g., head 16 of the fastener 4 in FIG. 1), such that both the fasteners and the female hook components can accommodate the same tulip assemblies. This allows a surgeon to easily apply different types of modular tulip assemblies, such as polyaxial or uniplanar, to both the fasteners and hook components during surgery. In some embodiments, the head of one or more fasteners have the same or similar shape and diameter as the head portion of one or more hook components.

In some embodiments, a surgical method is performed utilizing a surgical system having one or more fasteners (e.g., pedicle screws) in addition to one or more hook components. Additional components, such as transverse connectors and rod members can also be used. In some embodiments, a surgeon will implant a pair of fasteners into bone members, such as the pedicles. Before or after implantation of the fasteners, the surgeon can hook a male hook component onto a bone member. The surgeon can then attach a female hook component onto the male hook component. The female hook component is capable of translating and rotating relative the male hook component. Once the female hook component is hooked onto a bone member and positioned in a desired position relative to the male hook component, the female hook component is capable of being locked thereon. The female hook component can be locked relative to the male hook component, for example, by tightening a set screw on the head portion of the female hook component. With the fasteners and hook components in place, the surgeon can then apply one or more modular tulip assemblies on one or more of the fasteners and hook components. Advantageously, the one or more modular tulip assemblies can be used for both the fasteners and the hook members. In addition, the modular tulip assemblies are capable of easy removal and replacement should the surgeon desire to make changes in situ (e.g., the surgeon can easily replace a polyaxial tulip assembly with a uniplanar tulip assembly if desired in situ). With the tulip assemblies in place, the surgeon can then insert one or more rod members through the tulip assemblies to assist in providing a stabilization system to the vertebrae.

Figure 43:
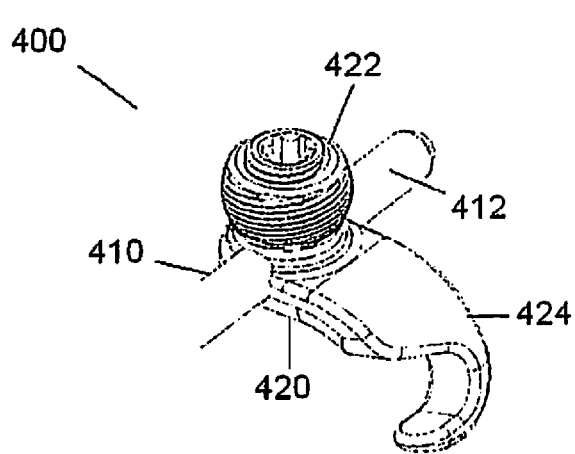
FIG. 43 illustrates a top perspective view of an alternative hook system in accordance with embodiments of the present application.

FIG. 43 illustrates a top perspective view of an alternative hook system in accordance with embodiments of the present application. Like the hook system in FIG. 42A, the hook system 400 in FIG. 43 includes a male hook component 410 and a female hook component 420, whereby the female hook component 420 includes a head member 422 and a hook member 424 and is capable of translational and rotational movement relative to the male hook component 410. However, in the present embodiment, the hook member 424 of the female hook component 420 is laterally offset from the head member 422. In other words, unlike the hook member 424 that is directly below the head member 422 (as shown in FIG. 42A), the hook member 424 in the present embodiment is below but off to the side of the head member 422.

Such a female hook component 420 can advantageously be used to grip a bone member that is laterally offset from the head member 422.

Figure 44:
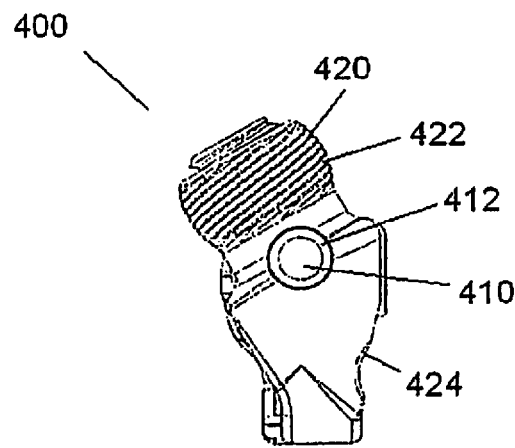
FIG. 44 illustrates a front view of an alternative hook system in accordance with embodiments of the present application.

FIG. 44 illustrates a front view of an alternative hook system in accordance with embodiments of the present application. Like the hook system in FIG. 42A, the hook system 400 in FIG. 44 includes a male hook component 410 and a female hook component 420, whereby the female hook component 420 includes a head member 422 and a hook member 424 and is capable of translational and rotational movement relative to the male hook component 410. However, in the present embodiment, the head member 422 of the female hook component 420 is angularly oriented. In other words, unlike the hook member 424 that has a central longitudinal that is transverse to rod member 412 (as shown in FIG. 42A), the hook member 424 in the present embodiment has a central longitudinal axis that would be at an angle relative to the rod member 412. Such a female hook component 420 can advantageously be used to receive a tulip assembly at a different angle than a non-angled female hook component, which is beneficial in order to accommodate patients with different anatomies. Advantageously, the female hook members in FIGS. 43 and 44 can accommodate different rod placements, whether they are placed more medially or laterally. In addition, these designs can accommodate different spinal anatomies and locations such as the laminas and transverse processes.

Figure 45:
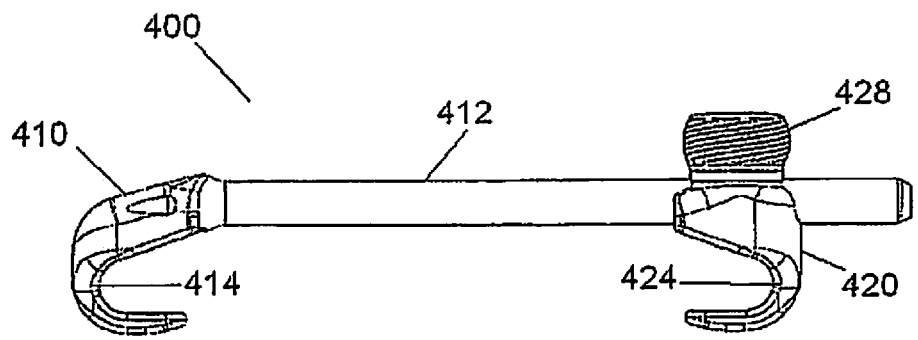
FIG. 45 illustrates a side view of an alternative hook system in accordance with embodiments of the present application.

FIG. 45 illustrates a side view of an alternative hook system in accordance with embodiments of the present application. In the present embodiment, the rod member 412 of the male hook component is exceptionally long. In some embodiments, the rod member 412 has a length that is 2.5, 3, 4 or more times greater than the length of the female hook component 420. By providing a rod member 412 that is exceptionally long, the hook system can be advantageously used for more than one level of the spine as part of a fusion construct.

Figure 46A:
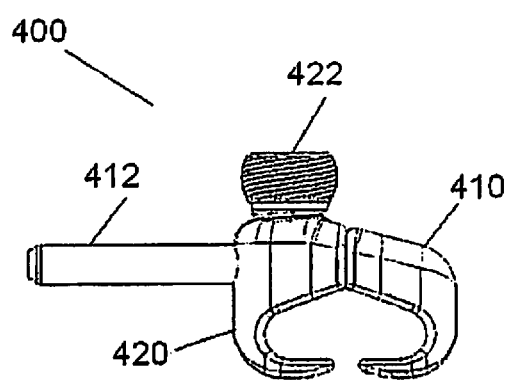
FIGS. 46A and 46B illustrate side views of an alternative hook system in accordance with embodiments of the present application.
Figure 46B:
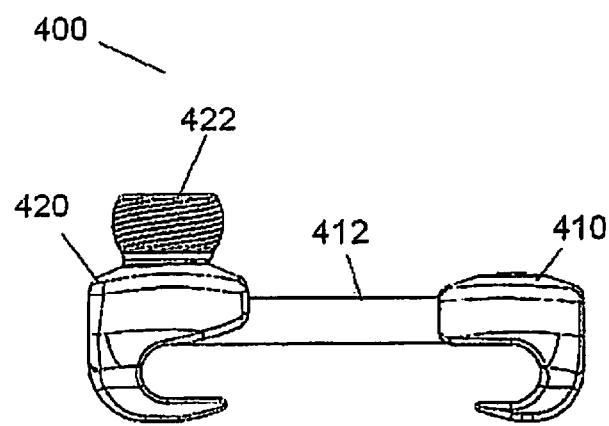

FIGS. 46A and 46B illustrate side views of an alternative hook system in accordance with embodiments of the present application. Like prior hook systems, the hook system of the present embodiment includes a male hook component 410 and a female hook component 420, whereby the female hook component 420 includes a head member 422 and a hook member 424 and is capable of translational and rotational movement relative to the male hook component 410. However, in the present embodiment, the head member 422 of the female hook component 420 serves as the locking mechanism such that no other component (e.g., set screw) is needed. In other words, once the female hook component 420 has been placed in a desired translational and rotational orientation relative to the male hook component 410, the female hook component 420 can be locked simply by rotating the head member 422. The head member 422 of the female hook component 420 can serve as its own set screw, and thereby apply downward pressure on the rod member 412 of the male hook component 410, thereby locking the system. Advantageously, the hook systems described herein provide a low profile design that help to provide additional stability and enable a rigid fusion.

Figure 50:
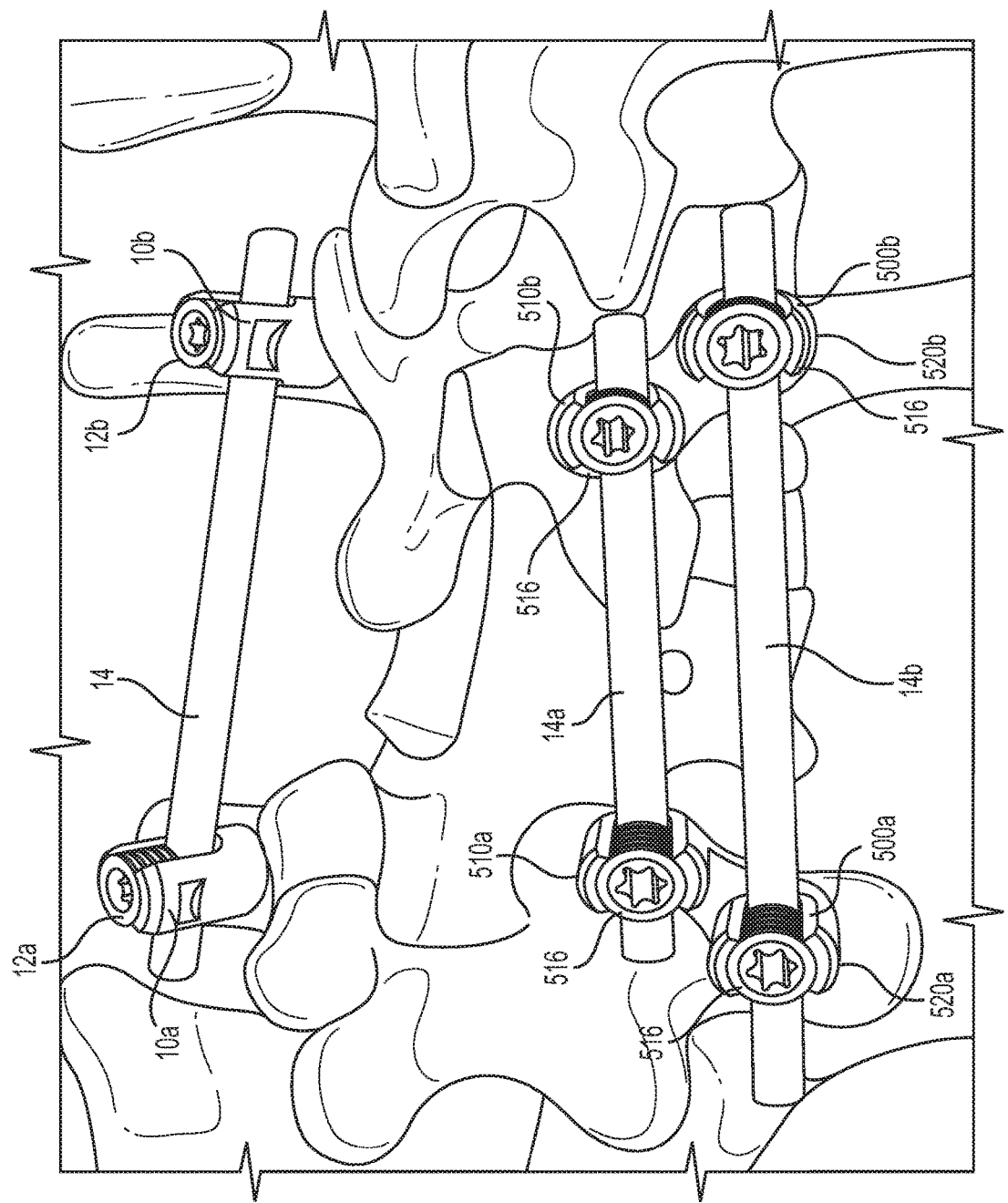
FIG. 50 illustrates a spinal stabilization system utilizing one or more modular double tulip assemblies in accordance with embodiments of the present application.

FIGS. 47-50 illustrate different embodiments of a modular double tulip assembly in accordance with embodiments of the present application. The modular double tulip assembly 500 can receive two side-by-side rods such that a dual rod construct can be formed between two or more modular double tulip assemblies, as shown in FIG. 50. Advantageously, when used in a spinal stabilization construct, the modular double tulip assembly 500 can provide increased strength and stiffness to a particular area of the construct (e.g., where an osteotomy has been performed). Furthermore, due to its modularity, the modular double tulip assembly 500 can easily be used to replace a single tulip assembly (as shown in FIG. 1), if a revision surgery is required, without having to remove a screw or fastener 4.

Figure 47:
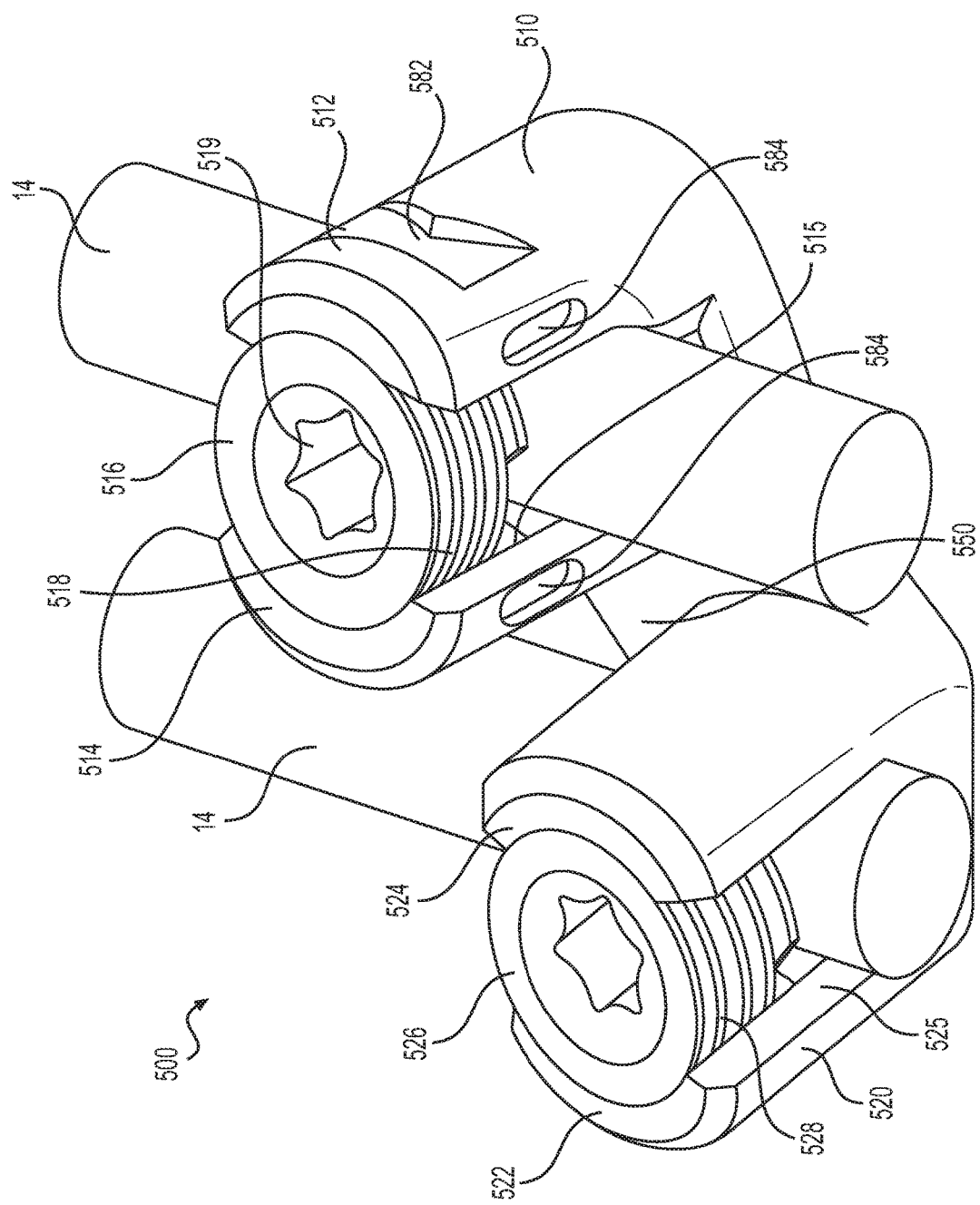
FIG. 47 illustrates a top perspective view of a modular double tulip assembly in accordance with embodiments of the present application.

FIG. 47 illustrates a top perspective view of a modular double tulip assembly in accordance with embodiments of the present application. The modular double tulip assembly 500 can comprise a first tulip element 510 and a second tulip element 520 that are connected to one another via a connecting element or bridge 550. Each of the tulip elements 510, 520 is configured to receive a stabilization member or rod 14 therethrough, thereby advantageously forming a dual-rod construct (as shown in FIG. 50). However, first tulip element 510 can be distinct from the second tulip element 520. For example, the first tulip element 510 can be modeled similarly to the tulip assembly in FIG. 1, and therefore can be received modularly over a bone screw or fastener that is inserted in bone. In contrast, the second tulip element 520 does not need to be inserted over a bone fastener, and thus includes different features, as will be discussed in more detail below. In other embodiments, the first tulip element 510 is similar to the second tulip element 520 such that both share most if not all features. For example, in some embodiments, both the first tulip element 510 and the second tulip element 520 can be modularly received over a bone screw.

In some embodiments, the first tulip element 510 can be similarly modeled after the modular single tulip assembly shown in FIG. 1. The first tulip element 510 can include a first extension or arm 512 and a second extension or arm 514. A U-shaped channel extends through the pair of arms 512, 514 and is capable of receiving a rod member 14 therethrough. While not shown in FIGS. 47-50, the first tulip element 510 can include a clamp element 7 and a wedge element 8 (as shown in FIG. 1) therein, thereby allowing the first tulip element 510 to be modularly placed over a bone fastener. Once the first tulip element 510 is modularly placed over a bone fastener, the rod member 14 can be placed within the first tulip element 510, and a locking cap assembly 516 can be delivered over the rod member 14. In some embodiments, the locking cap assembly 516 can be similar to the locking cap assembly 12 in FIG. 1, while in some embodiments (such as in FIGS. 47-50) the locking cap assembly 516 is different. For example, in the present embodiment, the locking cap assembly 516 includes more threads from its upper surface to its lower surface, and is primarily threaded into matching inner threads 515 formed within the walls of the arms 512, 514.

As shown in FIG. 47, the first tulip element 510 includes one or more tool engagement features 582, 584. One or more side tool engagement features 582 can be formed on the outer surfaces of the arms 512, 514. Similarly, one or more front or rear tool engagement features 584 can be formed on the front or rear surfaces of the arms 512, 514. As shown in FIG. 47, the one or more side tool engagement features 582 are of a different shape from the one or more front or rear tool engagement features 584. In some embodiments, the one or more side tool engagement features 582 can form a channel that extends along a majority of the width of the arms 512, 514. In some embodiments, the one or more front or rear tool engagement features 584 are of a much smaller width relative to the side tool engagement features 582. These engagement features 584 can be elliptical or oval, as shown in FIG. 47. The instruments that can engage the one or more tool engagement features 582, 584 vary and can include insertion instruments, rod reduction instruments, and derotation instruments. In some embodiments, the instruments that engagement the tool engagement features 582, 584 are multi-purpose instruments (e.g., for rod reduction and derotation).

In some embodiments, the second tulip element 520 can include a first extension or arm 522 and a second extension or arm 524. The arms 522, 524 form a U-shaped channel for receiving a rod member 14 and a locking cap assembly 526 therethrough, thereby forming part of a modular double tulip assembly. Unlike the first tulip element 510, the second tulip element 520 need not be received modularly over a bone screw or fastener, and therefore does not include a clamp element 7 or wedge element 8 (as shown in FIG. 1) therein. Instead, the second tulip element 520 comprises a lower base portion 527 (shown in FIGS. 48 and 49) for simply receiving the rod member 14 therein. As shown in FIG. 49, unlike the first tulip element 510 that includes an aperture or opening 517 for receiving a bone fastener therein, the second tulip element 520 need not include such an aperture or opening, as it need not be received modularly over a bone fastener. In other embodiments, the second tulip element 520 can be similar in form to the first tulip element 510 and can be received modularly over a bone fastener if desired.

As shown in FIG. 47, the second tulip element 520 does not include the tool engagement features 582, 584 as can be found on the first tulip element 510. Rather, the arms 522, 524 of the second tulip element 520 are smooth and without tool engagement features. While certain instruments may still be used with the second tulip element 520, the same tools that engage the tool engagement features 582, 584 of first tulip element 510 will not engage such features in the second tulip element 520. In other embodiments, the second tulip element 520 can include the same or similar tool engagement features 582, 584 as first tulip element 510, such that the same tools can engage the second tulip element 520 as well as the first tulip element 510.

Advantageously, the arms 512, 514 of the first tulip element 510 are completely separate and independent from the arms 522, 524 of the second tulip element 520. As shown in FIG. 47, none of the arms 512, 514, 522, 524 share an upward surface with another arm. Even the second arm 514 of the first tulip element 510 and the second arm 524 of the second tulip element 520 (which are the two closest arms between the tulip elements) have a gap or space between the two arms 514, 524. By providing such a space between the two arms 514 and 524, this advantageously allows one or more instruments or tools to grasp or grab either of the first tulip element 510 or the second tulip element 520. For example, a reduction tool can easily grab the inner and/or outer surfaces of the first and second arms 512, 514 of the first tulip element 510 without any interference from the arms 522, 524 of the second tulip element 520, as the arms 512, 514 of the first tulip element 510 are independent from and spaced apart from the arms 522, 524 of the second tulip element 520.

As shown in FIG. 47, a bridge member 550 extends between the first tulip element 510 and the second tulip element 520. The bridge member 550 is formed between a bottom portion or base of the first tulip element 510 and a bottom portion or base of the second tulip element 520.

FIG. 48 illustrates a front view of the modular double tulip assembly of FIG. 47 in accordance with embodiments of the present application. From this view, one can see how the first tulip element 510 is distinguishable from the second tulip element 520. In particular, the first tulip element 510 is structurally different from the second tulip element 520. While the first tulip element 510 is capable of modular attachment over a bone fastener, and therefore includes features such as wedge element 8 having an open bore 50 for receiving the fastener therein, the second tulip element 520 need not include such features. Moreover, while the first tulip element 510 is substantially or completely vertical, the second tulip element 520 is angled. In some embodiments, the second tulip element 520 can have an angle relative to a vertical axis of between 0 and 40 degrees, and more particularly, between 15 and 20 degrees. The advantage of having the second tulip element 520 angled is that it is angled with respect to the sagittal plane and therefore allows for a more lateral introduction of a rod therein if desired.

While FIG. 48 shows a modular double tulip assembly whereby the first tulip element 510 is vertical and the second tulip element 520 is angled relative to the first tulip element 510 and a vertical axis, in other embodiments, both the first tulip element 510 and the second tulip element 520 can be straight and vertical relative to a vertical axis. In other embodiments, if desired, both the first tulip element 510 and the second tulip element 520 can be angled relative to a vertical axis.

FIG. 49 illustrates a top view of the modular double tulip assembly of FIG. 47 in accordance with embodiments of the present application. From this view, one can see how the first tulip element 510 is further distinguishable from the second tulip element 520. In particular, the first tulip element 510 is structurally different from the second tulip element 520. While the first tulip element 510 is capable of modular attachment over a bone fastener, and therefore includes features such as locking clamp assembly 6 (shown in FIG. 1) that leave an opening 517 through the first tulip element 510 for receiving a bone fastener, the second tulip element 520 need not include such features. Rather, as discussed above, the second tulip element 520 includes a lower base portion 527 that receives a rod and does not leave an opening therethrough for receiving a bone fastener.

FIG. 50 illustrates a spinal stabilization system utilizing one or more modular double tulip assemblies in accordance with embodiments of the present application. The spinal stabilization system includes a single rod construct that extends along a first side of one or more vertebral bodies and a dual rod construct that extends along an opposite side of the one or more vertebral bodies.

The single rod construct utilizes a first modular single tulip assembly 10a and a second modular single tulip assembly 10b, whereby a single rod 14 extends between the two tulip assemblies. Locking cap assemblies 12a and 12b can be lowered down onto each of the rods. In some embodiments, each of the first and second modular single tulip assemblies 10a, 10b can be modeled after the tulip assembly found in FIG. 1.

The dual rod construct is positioned on an opposite side of the one or more vertebrae from the single rod construct. Advantageously, the dual rod construct is provided to provide greater strength and stability to the side of the one or more vertebrae where additional bone has been removed (e.g., via an osteotomy). The dual rod construct utilizes a first modular double tulip assembly 500a and a second modular double tulip assembly 500b, whereby a pair of rods 14a, 14b extend between the two tulip assemblies. Locking cap assemblies 516 can be lowered down onto each of the rods. In some embodiments, each of the first and second modular double tulip assemblies 500a, 500b can be modeled after the tulip assembly found in FIG. 47.

From the view in FIG. 50, one can see how each of the double tulip assemblies 500a, 500b includes a pair of tulips, whereby one tulip is offset from the other. Double tulip assembly 500*a* includes a first tulip 510*a* and a second tulip 520*a* offset from the first tulip, while double tulip assembly 500*b* includes a first tulip 510*b* and a second tulip 520*b* offset from the second tulip. The offset feature of the double tulip assemblies 500*a*, 500*b* advantageously allows one tulip to be placed further in a cephalad-caudal direction than another tulip in the same assembly. This advantageously eases the ability of a surgeon to use an instrument on each of the individual tulips, by providing space between each of the tulips, even when part of the same assembly. For example, as shown in FIG. 50, in the first modular double tulip assembly 500*a*, the second tulip 520*a* is placed in a more cephalad direction relative to the first tulip 510*a*. Likewise, in the second modular double tulip assembly 500*b*, the second tulip 520*b* is placed in a more caudal direction relative to the first tulip 510*b*.

In some embodiments, a method is provided that can result in a spinal stabilization system having at least one dual rod construct as shown in FIG. 50. In some embodiments, the method comprises performing an optional osteotomy to remove bone from a spine; inserting a first fastener into a first vertebral body; inserting a second fastener into a second vertebral body; modularly applying a first double tulip assembly 500*a* having a pair of tulip elements 510*a*, 520*a* over the first fastener; modularly applying a second double tulip assembly 500*b* having a pair of tulip elements 510*b*, 520*b* over the second fastener; inserting a first rod 14*a* between the first double tulip assembly 500*a* and the second double tulip assembly 500*b*; inserting a second rod 14*b* between the first double tulip assembly 500*a* and the second double tulip assembly 500*b*; and downwardly depositing locking cap assemblies 12 over each of the tulip elements 510*a*, 520*a*, 510*b*, 520*b* to secure the rod members as part of a dual rod construct. As in FIG. 50, the dual rod construct can extend along one side of a spine, while a single rod construct can extend along an opposite side of the spine. In some embodiments, the spine can contain multiple dual rod constructs.

Figure 51:
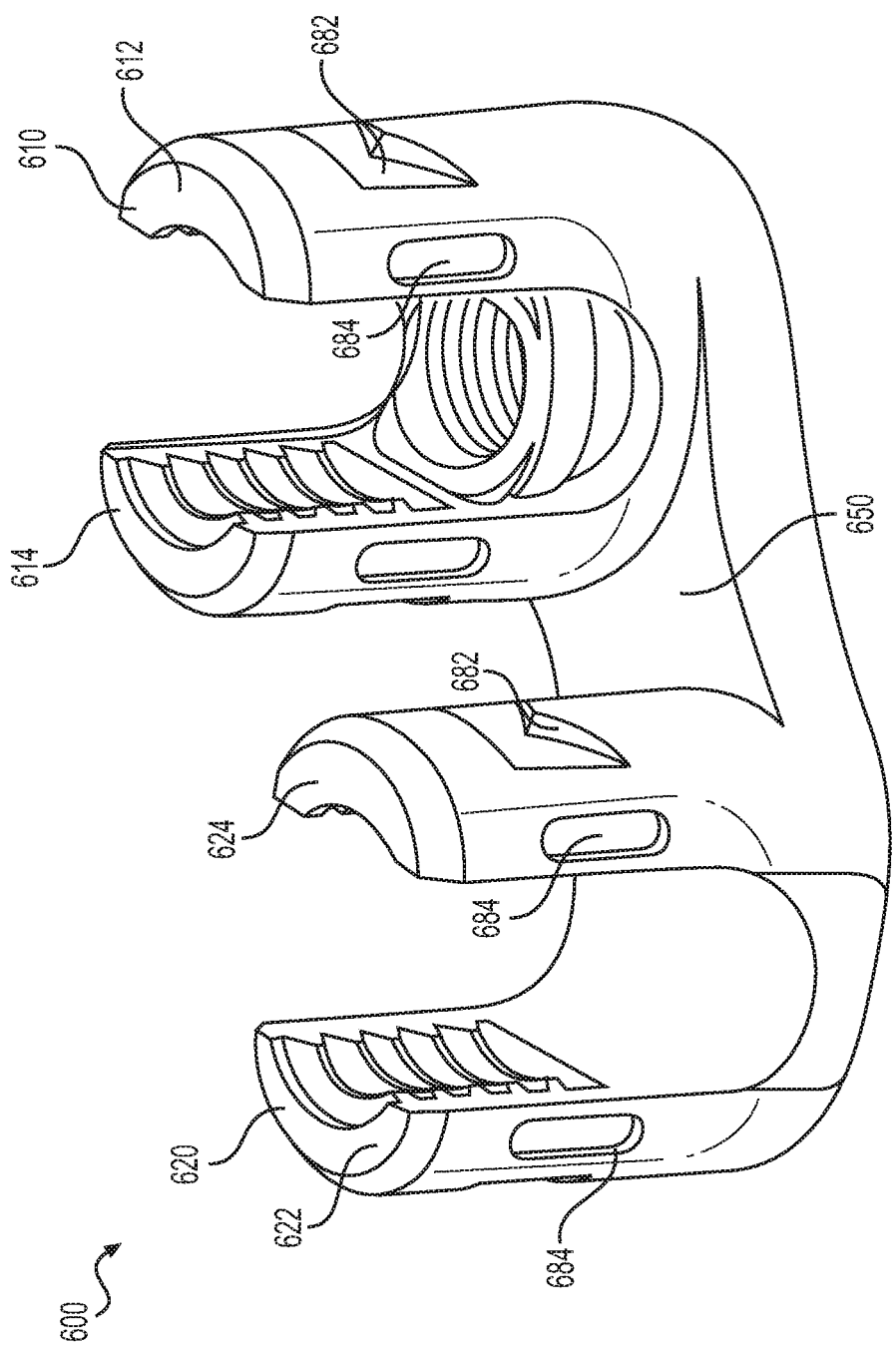
FIG. 51 illustrates a top perspective view of an alternative modular double tulip assembly in accordance with embodiments of the present application.

FIGS. 51-53 show different views of an alternative modular double tulip assembly in accordance with some embodiments. FIG. 51 shows a top perspective view of an alternative modular double tulip assembly, while FIG. 52 shows a front view and FIG. 53 shows a top view.

The modular double tulip assembly in FIGS. 51-53 shares a number of similar features to the modular double tulip assembly in FIGS. 47-49. In particular, the modular double tulip assembly 600 comprises a first tulip element 610 having a first arm 612 and a second arm 614 for receiving a first rod member therein and a second tulip element 620 having a first arm 622 and a second arm 624 for receiving a second rod member therein. Each of the arms 612, 614 of the first tulip element 610 are independent from the arms 622, 624 of the second tulip element 620. In fact, a space separates the second arm 614 of the first tulip element 610 from the second arm 624 of the second tulip element 620 (which are the closest arms between the first and second tulip elements), such that the arms of the first tulip element 610 do not share a wall with the arms of the second tulip element 620. In addition, the first tulip element 610 is connected to the second tulip element 620 via a connecting element or bridge 650.

The modular double tulip assembly in FIGS. 51-53 also includes some different features from the modular double tulip assembly in FIGS. 47-49. In particular, both the first tulip element 610 and the second tulip element 620 include one or more tool engagement features 682, 684. As shown in FIGS. 51 and 52, each of the tulip elements 610, 620 includes one or more side tool engagement features 682 and one or more front/rear tool engagement features 684. In addition, in contrast to embodiment in FIGS. 51-53 whereby the second tulip element 520 is at an angle relative to the first tulip element 510, in the present embodiment, both the first and second tulip elements 610, 620 are vertical and share a parallel longitudinal axis relative to one another. In addition, in the embodiment in FIGS. 51-53, the modular double tulip assembly 600 includes a lower surface 637 that is in part slanted. By providing a slanted lower surface 637, this advantageously helps the modular double tulip assembly 600 to avoid tissue or bone that may get in the way of the assembly during use.

Figure 55:
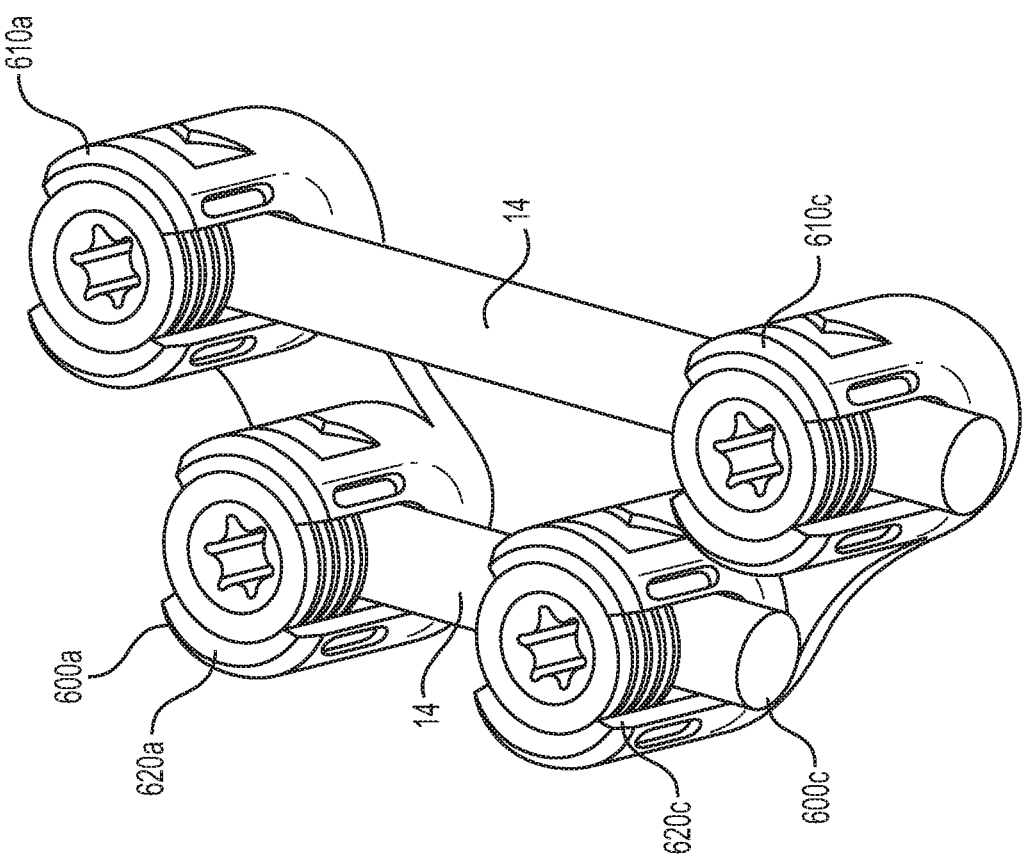
FIG. 55 illustrates an alternative dual rod construct using a pair of modular double tulip assemblies in accordance with embodiments of the present application.
Figure 54:
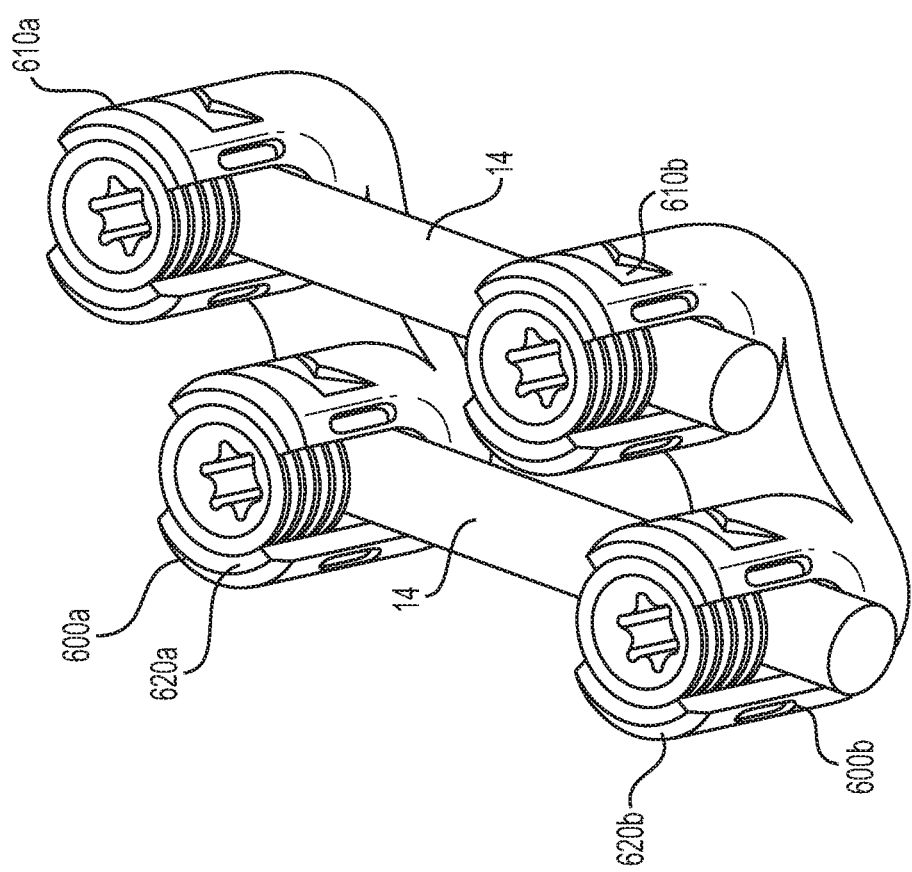
FIG. 54 illustrates a dual rod construct using a pair of modular double tulip assemblies in accordance with embodiments of the present application.

FIGS. 54 and 55 are two separate embodiments utilizing modular double tulip assemblies for dual rod constructs in accordance with some embodiments. In FIG. 54, a pair of modular double tulip assemblies 600*a* and 600*b* is used to hold two rods 14. Double tulip assembly 600*a* is the same as double tulip assembly 600*b*. In addition, both are oriented similarly. In FIG. 55, a pair of modular double tulip assemblies 600*a* and 600*c* is used to hold two rods 14 as well. However, the modular double tulip assemblies 600*a* and 600*b* are mirror-images of one another. In other words, the modular double tulip assembly 600*a* could be used, for example, on a left side of a spine, while modular double tulip assembly 600*c* could be used, for example, on a ridge side of a spine. In the embodiment in FIG. 55, the modular double tulip assemblies 600*a* and 600*c* could be used on the same side of a vertebral body, with tulip elements 620*a* and 620*c* being a closer distance than tulip elements 610*a* and 610*c*. By providing tulip elements 620*a* and 620*c* that are close together, this advantageously helps to strengthen the rod 14 in that area, which could be beneficial in the event that greater strength is required (e.g., such as in an osteotomy or in a tumor removal procedure). The embodiments shown in FIGS. 54 and 55 show how different dual rod constructs can advantageously be created by using different types of modular double tulip assemblies.

Advantageously, by using the modular double tulip assemblies described above, a surgeon can strengthen a spine stabilization construct by providing dual rods along at least a portion of the construct. In addition, as the modular double tulip assemblies are modular, the assemblies can be used to easily replace single tulip assemblies or other double tulip assemblies with ease.

FIGS. 56-64 illustrate different embodiments of a pre-assembled double tulip assembly 700 in accordance with embodiments of the present application. The double tulip assembly 700 can receive two side-by-side rods such that a dual rod construct can be formed between two or more double tulip assemblies. When used in a spinal stabilization construct, the double tulip assembly 700 can provide increased strength and stiffness to a particular area of the construct (e.g., where an osteotomy has been performed). In general operation, the tulip assembly 700 is pre-assembled with a first tulip element 710, a second tulip element 720, a bridge 750, a bone fastener 704, saddle 706, and a ring 708. Tulip elements 710 and 720 may be spaced apart or disposed close together.

Figure 56:
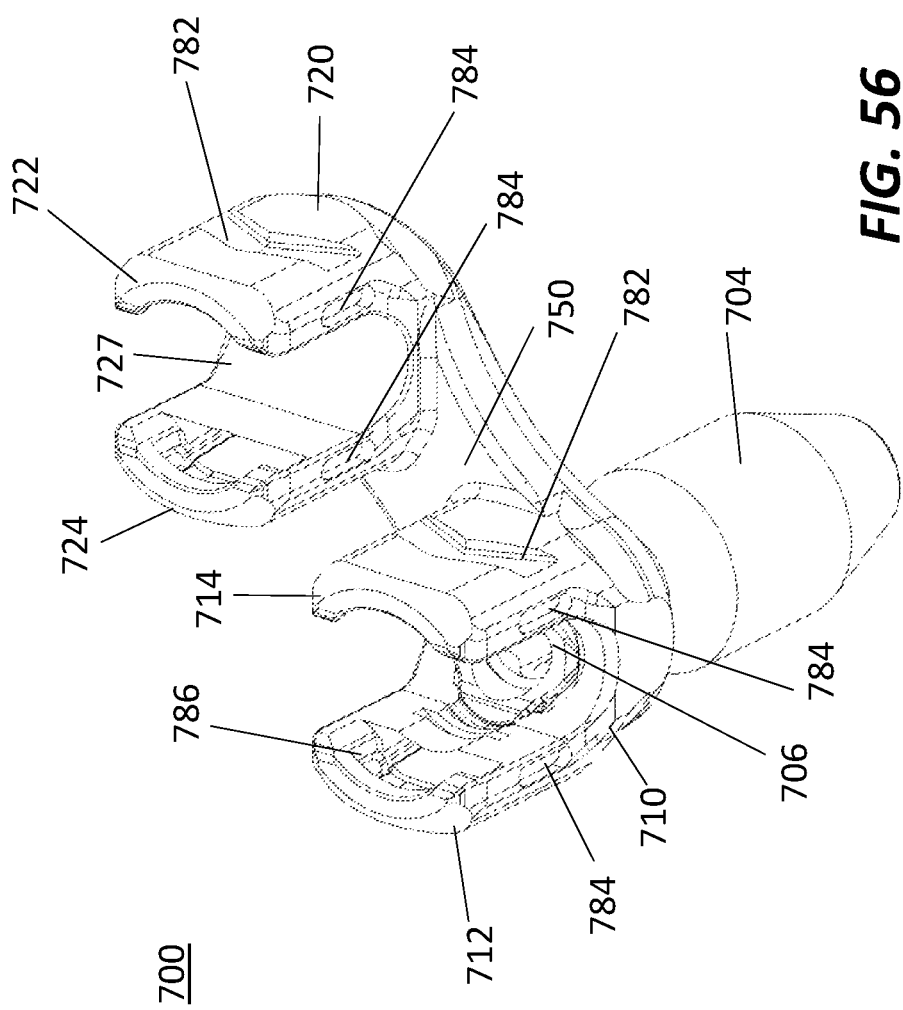
FIG. 56 illustrates a top view of an alternative dual rod construct using a pre-assembled double headed tulip assembly in accordance with embodiments of the present disclosure.

FIG. 56 illustrates a top perspective view of a pre-assembled double tulip assembly 700 in accordance with embodiments of the present application. The double tulip assembly 700 can comprise a first tulip element 710 and a second tulip element 720 that are connected to one another via a connecting element or bridge 750. Each of the tulip elements 710, 720 is configured to receive a stabilization member or rod 14 therethrough, thereby advantageously forming a dual-rod construct. First tulip element 710 can be distinct from the second tulip element 720. For example, the first tulip element 710 may contain saddle 706 and ring 708 and be configured to receive and secure bone fastener 704. In contrast, the second tulip element 720 does not need to be attached to the bone fastener, and thus may include different features. In other embodiments, the first tulip element 710 is similar to the second tulip element 720 such that both share most if not all features.

The first tulip element 710 can include a first extension or arm 712 and a second extension or arm 714. A U-shaped channel extends through the pair of arms 712, 714 and is capable of receiving a rod member 14 therethrough. The first tulip element 710, via saddle 706 and ring 708 therein, may allow the first tulip element 710 to be attached to bone fastener 704. The rod member 14 can be placed within the first tulip element 710, and a locking cap assembly can be delivered over the rod member 14. In some embodiments, the locking cap assembly can be similar to the locking cap assembly 12 in FIG. 1 or locking cap assembly 716 in FIG. 47.

As shown in FIG. 56, the first tulip element 710 includes one or more tool engagement features 782, 784. One or more side tool engagement features 782 can be formed on the outer surfaces of the arms 712, 714. Similarly, one or more front or rear tool engagement features 784 can be formed on the front or rear surfaces of the arms 712, 714. As shown in FIG. 56, the one or more side tool engagement features 782 are of a different shape from the one or more front or rear tool engagement features 784. In some embodiments, the one or more side tool engagement features 782 can form a channel that extends along a majority of the width of the arms 712, 714. In some embodiments, the one or more front or rear tool engagement features 784 are of a much smaller width relative to the side tool engagement features 782. These engagement features 784 can be elliptical or oval, as shown in FIG. 56. The instruments that can engage the one or more tool engagement features 782, 784 vary and can include insertion instruments, rod reduction instruments, and derotation instruments. In some embodiments, the instruments that engagement the tool engagement features 782, 784 are multi-purpose instruments (e.g., for rod reduction and derotation).

In some embodiments, the second tulip element 720 can include a first extension or arm 722 and a second extension or arm 724. The arms 722, 724 form a U-shaped channel for receiving a rod member 14 and a locking cap assembly therethrough. Unlike the first tulip element 710, the second tulip element 720 need not engage a bone screw or fastener, and therefore does not include a saddle 706 or ring 708 therein. Instead, the second tulip element 720 comprises a lower base portion 727 for receiving the rod member 14 therein. Unlike the first tulip element 710 that includes an aperture or opening 717 for receiving a bone fastener therein, the second tulip element 720 need not include such an aperture or opening, as it need not engage a bone fastener. In other embodiments, the second tulip element 720 can be similar in form to the first tulip element 710 and engage a bone fastener if desired.

FIG. 56 depicts the second tulip element 720 with similar tool engagement features as the first tulip element 710, however, the second tulip element 720 does not need to have the tool engagement features. Arms 722, 724 of the second tulip element 720 may be smooth and without tool engagement features.

Arms 712, 714 of the first tulip element 710 may be separate and independent from the arms 722, 724 of the second tulip element 720. As shown in FIG. 56, in one embodiment, none of the arms 712, 714, 722, 724 share an upward surface with another arm. Even the second arm 714 of the first tulip element 710 and the second arm 724 of the second tulip element 720 (which are the two closest arms between the tulip elements) have a gap or space between the two arms 714, 724. By providing such a space between the two arms 714 and 724, this advantageously allows one or more instruments or tools to grasp or grab either of the first tulip element 710 or the second tulip element 720. For example, a reduction tool can easily grab the inner and/or outer surfaces of the first and second arms 712, 714 of the first tulip element 710 without any interference from the arms 722, 724 of the second tulip element 720, as the arms 712, 714 of the first tulip element 710 are independent from and spaced apart from the arms 722, 724 of the second tulip element 720. FIGS. 60-64 show an alternative embodiment wherein the first and second tulip elements are disposed closer together.

As shown in FIG. 56, a bridge member 750 extends between the first tulip element 710 and the second tulip element 720. The bridge member 550 is formed between a bottom portion or base of the first tulip element 710 and a bottom portion or base of the second tulip element 720.

Figure 57:
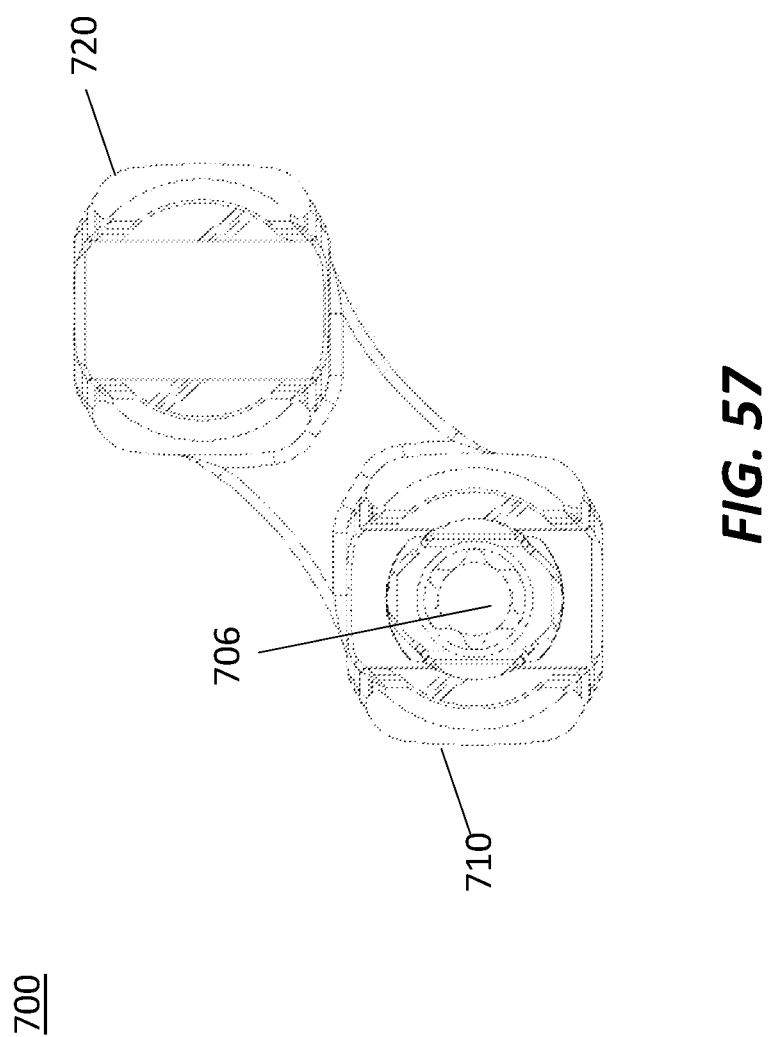
FIG. 57 illustrates a top view of the dual rod construct using a pre-assembled double headed tulip assembly of FIG. 56 in accordance with embodiments of the present disclosure.
Figure 58:
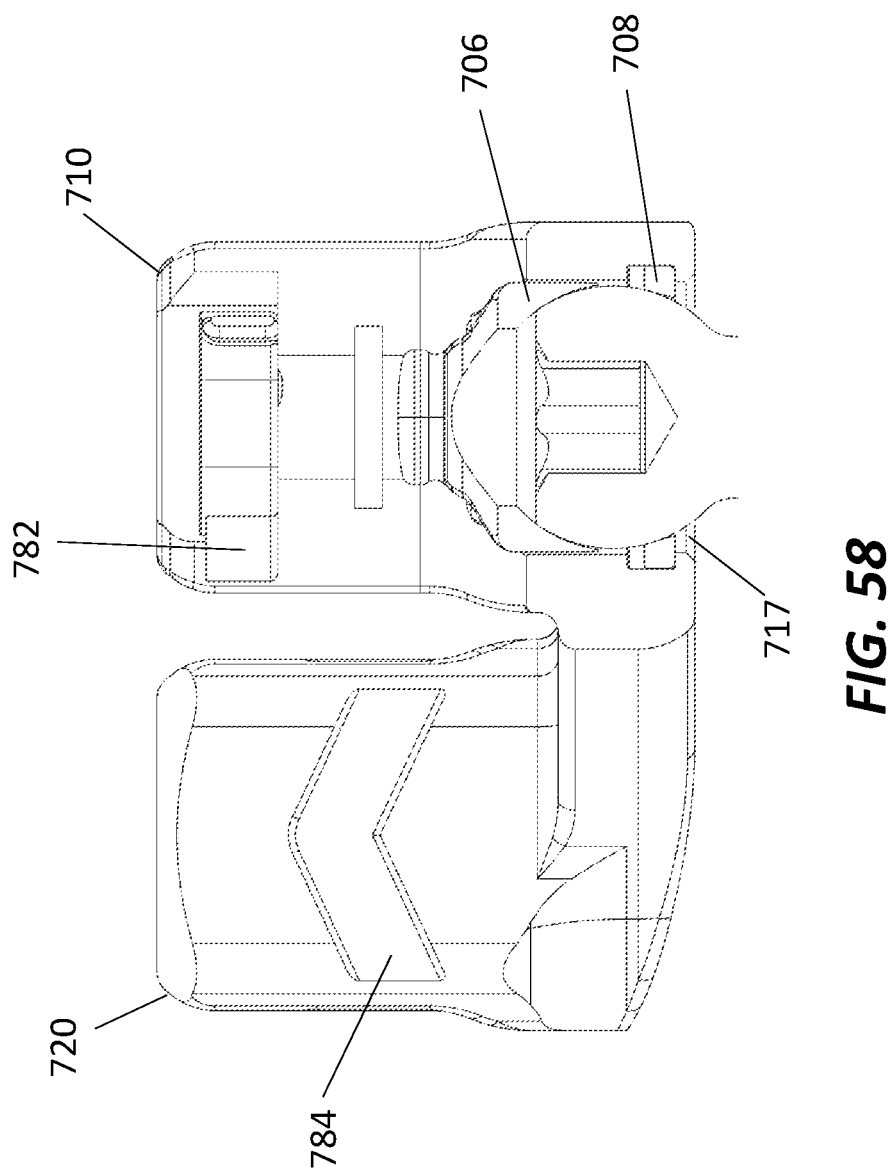
FIG. 58 illustrates a side view of the dual rod construct using a pre-assembled double headed tulip assembly of FIG. 56 in accordance with embodiments of the present disclosure.
Figure 60:
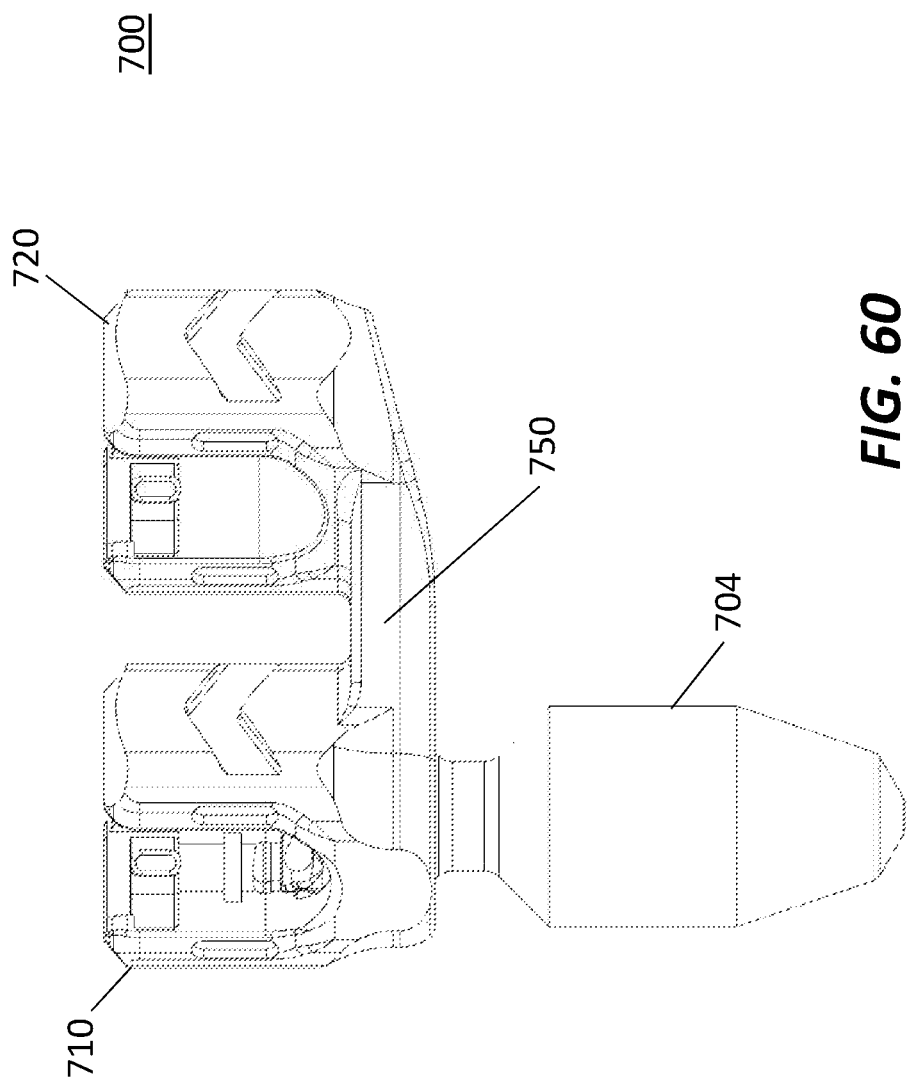
FIG. 60 illustrates a side view of the dual rod construct using a pre-assembled double headed tulip assembly of FIG. 56 in accordance with embodiments of the present disclosure.
Figure 61:
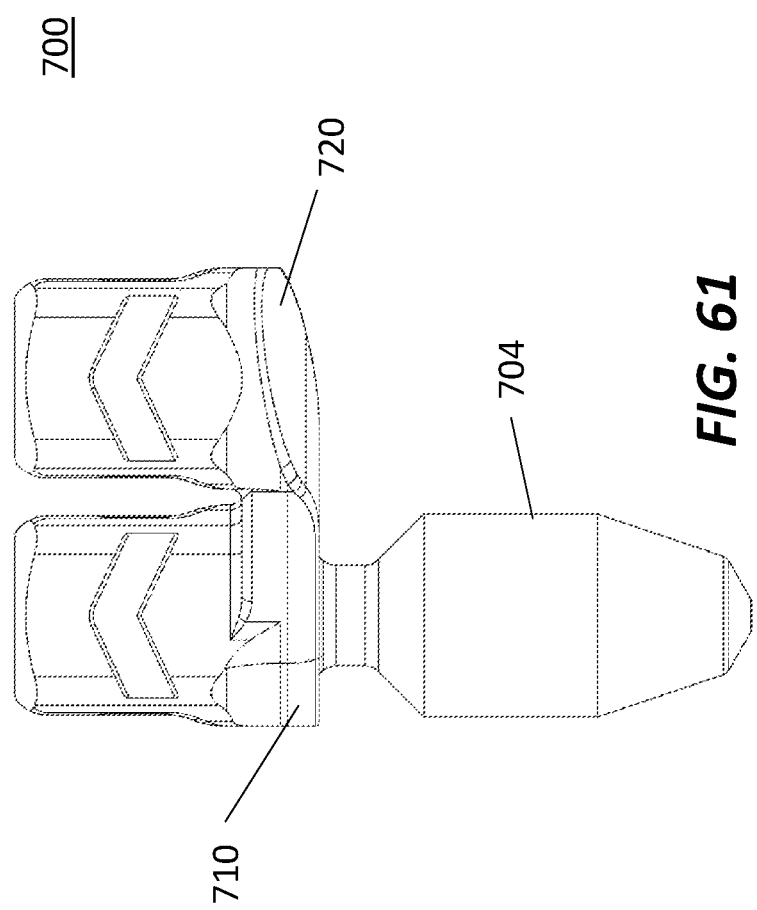
FIG. 61 illustrates a side view of the dual rod construct using a pre-assembled double headed tulip assembly of FIG. 56 in accordance with embodiments of the present disclosure.

FIG. 57 illustrates a top view of the double tulip assembly of FIG. 56 in accordance with embodiments of the present application. FIGS. 58, 60, and 61 illustrate a side view of FIG. 56. The first tulip element 710 may be structurally different from the second tulip element 720. While the first tulip element 710 is capable of attachment to a bone fastener, and therefore includes features such as saddle 706 that leave an opening 717 through the first tulip element 710 for receiving a bone fastener, the second tulip element 720 need not include such features. Rather, as discussed above, the second tulip element 720 includes a lower base portion 727 that receives a rod and does not leave an opening therethrough for receiving a bone fastener.

First tulip element 710 and second tulip element 720 may be used in a spinal stabilization system utilizing one or more double tulip assemblies in accordance with embodiments of the present application. For example, first tulip element 710 and second tulip element 720 may be used instead of the modular tulip elements 510 and 520 as shown in FIG. 50. The spinal stabilization system includes a single rod construct that extends along a first side of one or more vertebral bodies and a dual rod construct that extends along an opposite side of the one or more vertebral bodies. The dual rod construct is positioned on an opposite side of the one or more vertebrae from the single rod construct. The dual rod construct may be provided to provide greater strength and stability to the side of the one or more vertebrae where additional bone has been removed (e.g., via an osteotomy). In addition, a dual rod construct may be used on both sides of one or more vertebral bodies.

Figure 59:
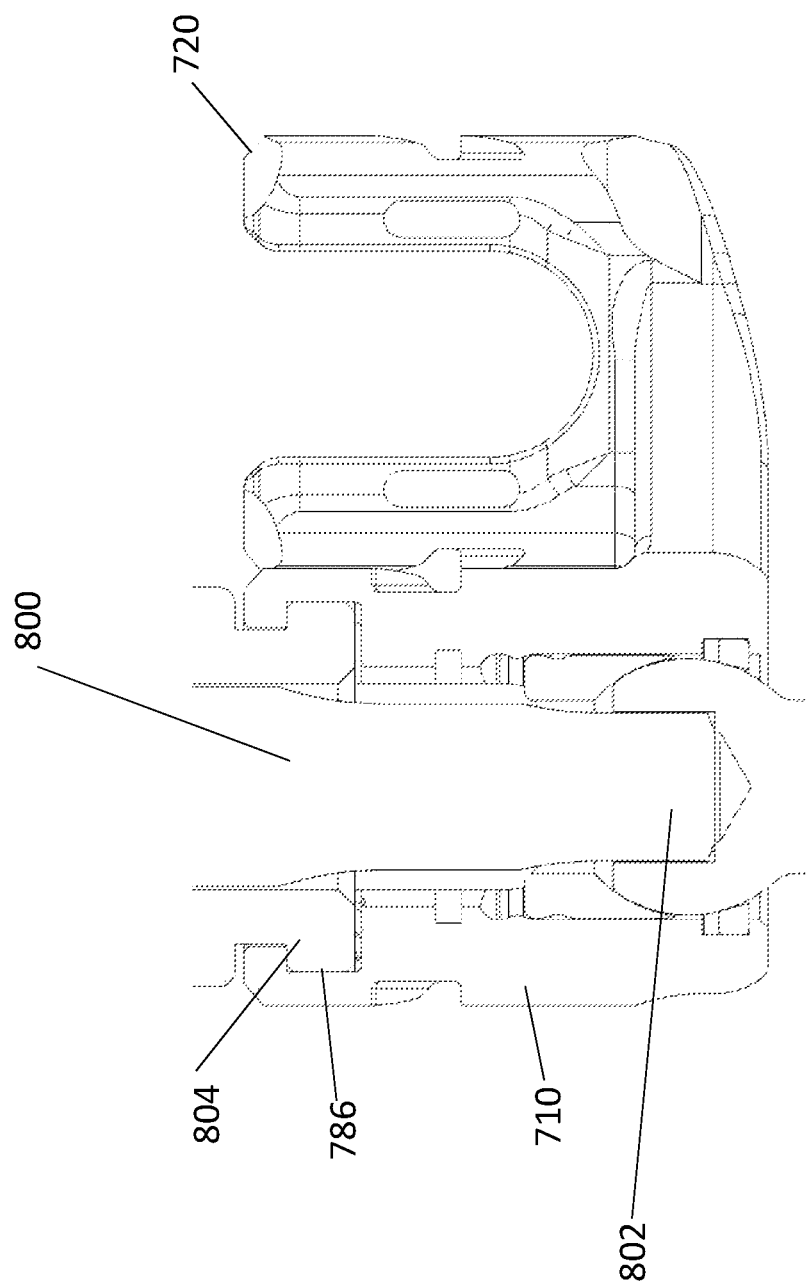
FIG. 59 illustrates a side view of the dual rod construct using a pre-assembled double headed tulip assembly of FIG. 56 in accordance with embodiments of the present disclosure.

FIG. 59 illustrates assembly 700 and a driver 800. Driver 800 may include tip 802 and tabs 804. Tabs 804 may engage first tulip element 710 in grooves 786 to lock driving mechanism 800 relative to the assembly 700. While tip 802 engages a proximal end of bone fastener 704, rotation of driver 800 advances or retracts bone fastener 704 into or out of a bone. During rotation, tabs 804 may lock the orientation of tulip assembly 700 preventing rotational movement of first tulip element 710 and second tulip element 720 relative to bone fastener 704. In addition, instead of driver 800 having tabs that engage grooves inside the first tulip element, the driver may be configured to engage or mate with the outer surface of the tulip.

Figure 62:
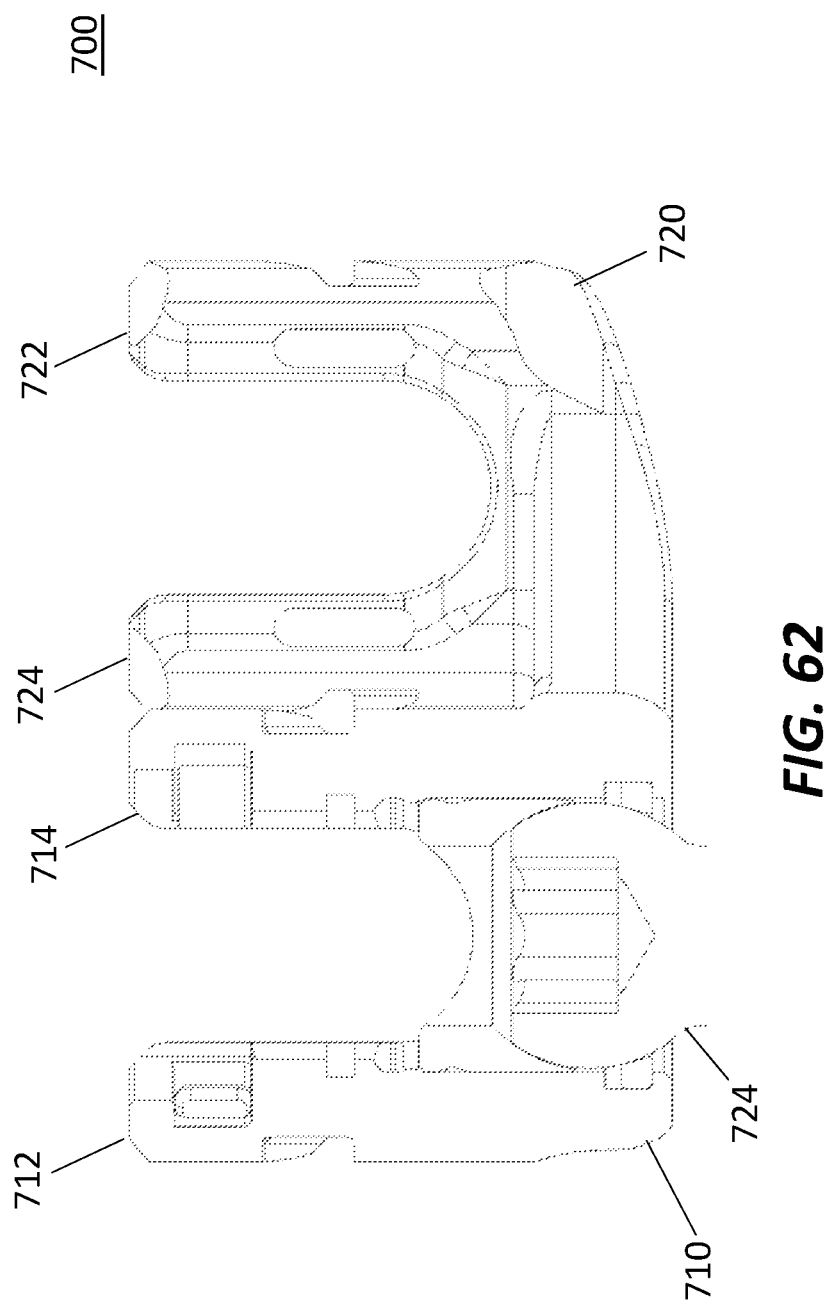
Figure 63:
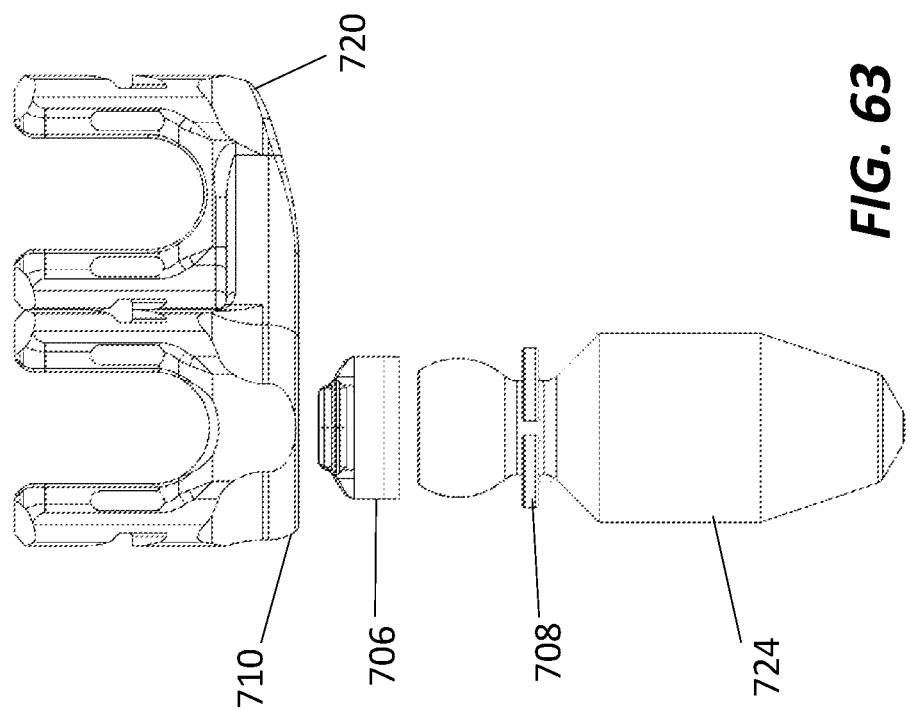

FIGS. 62-64 show different views of double tulip assembly 700 in accordance with the present disclosure. FIG. 62 shows the first and second tulip elements 710 and 720, in which tulip element 710 is attached to a bone fastener 704. FIG. 63 illustrates an exploded view of assembly 700, including tulip elements 710 and 720, saddle 706, ring 708 and bone fastener 704. FIG. 64 illustrates assembly 700 in a pre-assembled configuration including tulip elements 710 and 720, saddle 706, ring 708 and bone fastener 704.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A pre-assembled spine stabilization system configured to be implanted into adjacent vertebral bodies, said system comprising:
    a first bone fastener;
    a second bone fastener;
    a first tulip assembly comprising a first tulip element, having a first saddle and a first ring, and a second tulip element, wherein the first tulip element of the first tulip assembly is configured to attach to the first bone fastener;
    a second tulip assembly comprising a first tulip element, having a second saddle and a second ring, and a second tulip element, wherein the first tulip element of the second tulip assembly is configured to attach to the second bone fastener;
    a first rod member that extends from the first tulip assembly to the second tulip assembly, wherein the first rod member is disposed on the first saddle and the second saddle; and
    a second rod member that extends from the first tulip assembly to the second tulip assembly,
    wherein the first bone fastener is retained in the first tulip assembly via the first ring and the second bone fastener is retained in the second tulip assembly via the second ring,
    wherein the first tulip assembly comprises a first bridge that extends between the first tulip element and the second tulip element of the first tulip assembly, and
    wherein the first bridge is formed between a bottom portion of the first tulip element and bottom portion of the second tulip element and configured to provide spacing between the first tulip element and the second tulip element.

2. The spine stabilization system of claim 1, wherein the first tulip element of the first tulip assembly comprises a first arm and a second arm and the second tulip element of the first tulip assembly comprises a first arm and a second arm.

3. The spine stabilization system of claim 2, wherein each of the arms of the first tulip assembly are independent from one another such that they do not share a wall.

4. The spine stabilization system of claim 1, wherein the second tulip element of the first tulip assembly is disposed parallel relative to the first tulip element of the first tulip assembly.

5. The spine stabilization system of claim 1, wherein the second tulip element of the first tulip assembly is offset at an angle relative to the first tulip element of the first tulip assembly.

6. The spine stabilization system of claim 1, wherein the first tulip element of the first tulip assembly has an exposed opening for receiving a bone fastener while the second tulip element of the first tulip assembly does not have an exposed opening for receiving a bone fastener.

7. The spine stabilization system of claim 1, wherein the first tulip element of the first tulip assembly has tool engagement features.

8. The spine stabilization system of claim 7, wherein the first tulip element of the first tulip assembly has one or more side tool engagement features.

9. The spine stabilization system of claim 8, wherein the first tulip element of the first tulip assembly has one or more front or rear tool engagement features that are on a different face from the one or more side tool engagement features.

10. A spine stabilization system comprising:
    a first bone fastener;
    a second bone fastener;
    a first tulip assembly comprising a first tulip element, having a first saddle and a first ring, wherein the first saddle is spaced from the first ring, and a second tulip element, wherein the first tulip element is configured to be received over the first bone fastener, wherein the first tulip element is separated from the second tulip element via a bridge, and wherein the first bone fastener is retained in the first tulip assembly by the first ring;
    a second tulip assembly comprising at least one tulip element, wherein the at least one tulip element is configured to attach to the second bone fastener; and
    a first rod member that extends from the first tulip assembly to the second tulip assembly,
    wherein the bridge is formed between a bottom portion of the first tulip element and bottom portion of the second tulip element and configured to provide spacing between the first tulip element and the second tulip element.

11. The spine stabilization system of claim 10, wherein the first tulip element of the first tulip assembly comprises a first arm and a second arm and the second tulip element of the first tulip assembly comprises a first arm and a second arm.

12. The spine stabilization system of claim 11, wherein each of the at least one tulip element of the second tulip assembly comprises a first arm and a second arm.

13. The spine stabilization system of claim 10, wherein the second tulip element of the first tulip assembly is at an angle relative to the first tulip element of the first tulip assembly.

14. The spine stabilization system of claim 10, wherein the second tulip element of the first tulip assembly is parallel relative to the first tulip element of the first tulip assembly.

15. The spine stabilization system of claim 10, wherein the first tulip element of the first tulip assembly comprises an opening through a lower surface for receiving the first bone fastener therethrough and the second tulip element of the first tulip assembly has no opening through a lower surface.

16. The spine stabilization system of claim 10, wherein the first tulip element of the first tulip assembly includes one or more side tool engagement features and the second tulip element of the first tulip assembly does not include any side tool engagement features.

17. The spine stabilization system of claim 10, wherein the first tulip element of the first tulip assembly includes one or more side tool engagement features and the second tulip element of the first tulip assembly also includes one or more side tool engagement features.

18. The spine stabilization system of claim 10, further comprising a first and second locking cap assembly downwardly deposited over the first and second tulip elements of the first tulip assembly.

19. The spine stabilization system of claim 10, wherein the second tulip assembly comprises a second ring to retain the second bone fastener.

* * * * *